US011682320B2

(12) United States Patent
Sadasivan et al.

(10) Patent No.: US 11,682,320 B2
(45) Date of Patent: Jun. 20, 2023

(54) CARDIAC SIMULATION DEVICE

(71) Applicant: Mentice, AB, Gothenburg (SE)

(72) Inventors: Chandramouli Sadasivan, Wilmington, DE (US); Baruch B. Lieber, Aventura, FL (US); Brandon Joseph Kovarovic, Croton-On-Hudson, NY (US); Louie E. Abejar, Centereach, NY (US); Henry Woo, Setauket, NY (US); David Jeffrey Carson, Stuart, FL (US); David Fiorella, East Setauket, NY (US); Michael Romeo, Port St. Lucie, FL (US); Gary Bunch, Northport, NY (US); Karl Keppeler, Manorville, NY (US)

(73) Assignee: Mentice, AB, Gothenburg (SE)

( * ) Notice: Subject to any disclaimer, the term of this patent is extended or adjusted under 35 U.S.C. 154(b) by 793 days.

(21) Appl. No.: 16/577,885

(22) Filed: Sep. 20, 2019

(65) Prior Publication Data
US 2020/0160753 A1 May 21, 2020

Related U.S. Application Data

(60) Provisional application No. 62/734,459, filed on Sep. 21, 2018.

(51) Int. Cl.
*G09B 23/30* (2006.01)
*G16H 50/50* (2018.01)
(Continued)

(52) U.S. Cl.
CPC ......... *G09B 23/303* (2013.01); *G09B 23/288* (2013.01); *G16H 50/20* (2018.01); *G16H 50/30* (2018.01); *G16H 50/50* (2018.01)

(58) Field of Classification Search
CPC ...... G09B 23/28; G09B 23/288; G09B 23/30; G09B 23/303; G16H 50/20; G16H 50/30; G16H 50/50
See application file for complete search history.

(56) References Cited

U.S. PATENT DOCUMENTS

| 2,684,684 A | 7/1954 | Stevenson |
| 3,376,660 A | 4/1968 | McGinnis |

(Continued)

FOREIGN PATENT DOCUMENTS

| JP | 2006276258 | 10/2006 |
| WO | WO2011094525 | 8/2011 |
| WO | WO2013116519 | 8/2013 |

OTHER PUBLICATIONS

Anonymous, "Endovascular surgery training-evaluation-simulation: EVE endovascular evaluator", FAIN-Biomedical, Inc., Japan, Internet article, http://www.fain-biomedical.com/fbm_wp/wp-content/themes/fbm_ns/images/pdf/eve_fbm_e.pdf, (retrieved Sep. 21, 2015).

(Continued)

*Primary Examiner* — Timothy A Musselman
(74) *Attorney, Agent, or Firm* — McHale & Slavin, P.A.

(57) ABSTRACT

A device and system for simulating normal and disease state cardiovascular functioning, including an anatomically accurate cardiac simulator for training and medical device testing. The system and device uses pneumatically pressurized chambers to generate ventricle and atrium contractions. In conjunction with the interaction of synthetic valves, which simulate mitral and aortic valves, the system is designed to generate pumping action that produces accurate volume fractions and pressure gradients of pulsatile flow, duplicating that of a human heart. Through the use of a control unit and sensors, one or more parameters, such as flow rates, fluidic pressure, and heart rate, may be automatically con- (Continued)

trolled, using feedback loop mechanisms to adjust parameters of the hydraulic system to simulate a wide variety of cardiovascular conditions including normal heart function, severely diseased or injured heart conditions, and compressed vasculature, such as hardening of the arteries.

30 Claims, 33 Drawing Sheets

(51) Int. Cl.
    *G16H 50/30*     (2018.01)
    *G16H 50/20*     (2018.01)
    *G09B 23/28*     (2006.01)

(56) References Cited

U.S. PATENT DOCUMENTS

| | | | |
|---|---|---|---|
| 3,434,162 A | 3/1969 | Wolfe | |
| 3,541,612 A | 11/1970 | Carney | |
| 3,755,825 A | 9/1973 | DeBakey et al. | |
| 3,916,449 A | 11/1975 | Davis | |
| 4,687,424 A | 8/1987 | Heimes | |
| 5,052,934 A | 10/1991 | Carey et al. | |
| 5,374,194 A | 12/1994 | Walcerz et al. | |
| 5,632,623 A | 5/1997 | Kolff et al. | |
| 5,634,797 A | 6/1997 | Montgomery | |
| 5,766,207 A | 6/1998 | Potter et al. | |
| 6,062,866 A | 5/2000 | Prom | |
| 6,146,325 A | 11/2000 | Lewis et al. | |
| 6,205,871 B1 | 3/2001 | Saloner et al. | |
| 6,234,804 B1 | 5/2001 | Yong | |
| 6,336,812 B1 | 1/2002 | Cooper et al. | |
| 6,461,165 B1 | 10/2002 | Takashina et al. | |
| 6,517,354 B1 | 2/2003 | Levy | |
| 6,685,481 B2 | 2/2004 | Chamberlain | |
| 6,790,043 B2 | 9/2004 | Aboud | |
| 6,843,145 B2 | 1/2005 | Jaszczak et al. | |
| 7,018,327 B1 | 3/2006 | Conti | |
| 7,021,940 B2 | 4/2006 | Morris et al. | |
| 7,063,942 B2 | 6/2006 | Dancu et al. | |
| 7,083,418 B2 | 8/2006 | Baldauf | |
| 7,569,809 B2 | 8/2009 | Vija et al. | |
| 7,798,815 B2 | 9/2010 | Ramphal et al. | |
| 7,866,983 B2 | 1/2011 | Hemphill et al. | |
| 7,976,312 B2 | 7/2011 | Eggert et al. | |
| 7,976,313 B2 | 7/2011 | Eggert et al. | |
| 8,016,598 B2 | 9/2011 | Eggert et al. | |
| 8,342,852 B2 | 1/2013 | King | |
| 8,608,484 B2 | 12/2013 | Kalafut et al. | |
| 8,632,343 B2 | 1/2014 | Blackburn | |
| 8,636,519 B2 | 1/2014 | Schwartz et al. | |
| 8,678,830 B2 | 3/2014 | Gurdin et al. | |
| 2002/0009386 A1 | 1/2002 | Lindsey | |
| 2003/0088151 A1 | 5/2003 | Kung et al. | |
| 2003/0220718 A1 | 11/2003 | Jaszczak et al. | |
| 2004/0033477 A1 | 2/2004 | Ramphal et al. | |
| 2004/0092789 A1 | 5/2004 | Tsukahara et al. | |
| 2004/0101814 A1 | 5/2004 | Morris et al. | |
| 2005/0084834 A1 | 4/2005 | Baldauf | |
| 2005/0100873 A1 | 5/2005 | Meythaler et al. | |
| 2005/0130107 A1 | 6/2005 | Ellington et al. | |
| 2008/0020362 A1 | 1/2008 | Cotin et al. | |
| 2009/0226867 A1 | 9/2009 | Kalafut et al. | |
| 2009/0246747 A1 | 10/2009 | Buckman, Jr. | |
| 2010/0167251 A1 | 7/2010 | Boutchko et al. | |
| 2011/0165546 A1 | 7/2011 | May | |
| 2012/0034586 A1 | 2/2012 | Gomo | |
| 2013/0132054 A1 | 5/2013 | Sharma et al. | |
| 2013/0196301 A1 | 8/2013 | Carson et al. | |
| 2016/0027345 A1* | 1/2016 | Carson | G09B 23/32 |
| | | | 434/262 |
| 2018/0018904 A1* | 1/2018 | Okayama | A61B 90/00 |
| 2021/0052328 A1* | 2/2021 | Sengupta | B33Y 80/00 |

OTHER PUBLICATIONS

Anonymous, "Comprehensive endovascular surgery simulation", FAIN-Biomedical, Inc., Japan, Internet article, http://www.japan-product.com/ads/fain-biomedical-inc, pp. 3-5, (retrieved Sep. 21, 2015).

Rotman, O. et al., "Novel polymeric valve for transcatheter aortic valve replacement applications: In Vitro hemodynamic study", Annals of Biomedical Engineering, Internet article: https://doi.org/10.1007/s10439-018-02119-7, pp. 1-13, (2018).

* cited by examiner

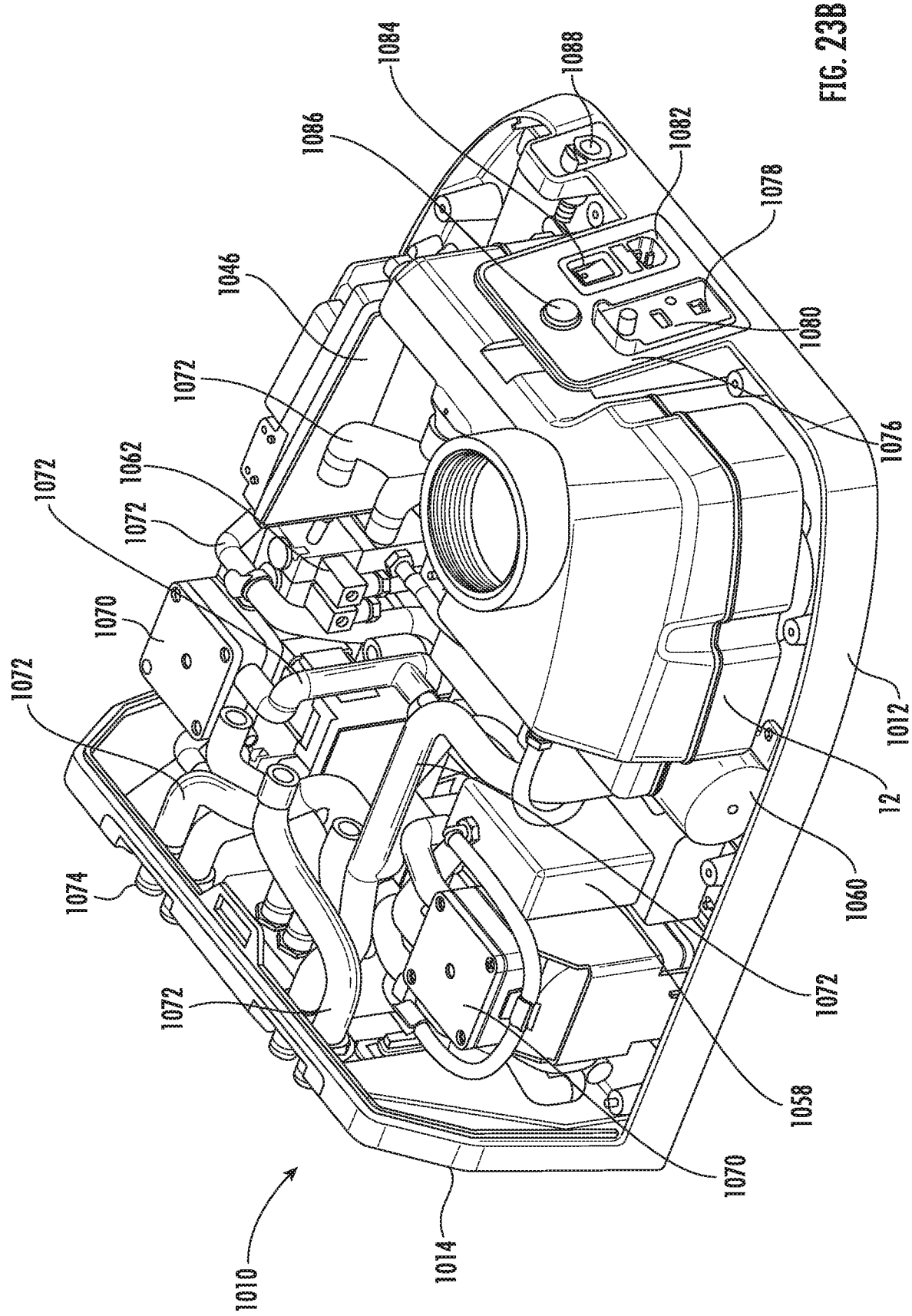

CARDIAC SIMULATION DEVICE

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 62/734,459, entitled "CARDIAC SIMULATION DEVICE", filed Sep. 21, 2018. The contents of the above referenced application are incorporated herein by reference in its entirety.

FIELD OF THE INVENTION

This invention relates to a surgical simulation system; to a device and system for simulating normal and disease state cardiovasculature functioning, including an anatomically accurate cardiac simulator for training and medical device testing; and more particularly, to a device and system for simulating normal and disease state cardiac functioning which uses sensors and other control mechanisms to automatically adjust hydraulic and/or pneumatic components of the system to achieve physiologically representative pressure and flow profiles.

BACKGROUND OF THE INVENTION

Cardiovascular disease, diseases affecting the heart and the vasculature, and vascular disease, diseases affecting the circulatory system are prevalent conditions affecting millions of individuals across the globe. While vasculature disease may manifest in the weakening, deformation, or hardening of arterial walls at a specific location, such disease state affects every organ in the human body. Several options exist to alleviate or minimize the risk associated with prolonged vasculature disease states. Depending on the severity, changes in life style, i.e. diet and increased exercise, or the use of drugs may be helpful. In situations where other options will not work or where the disease is severe, surgical intervention remains the primary treatment tool. Traditional surgical procedures have been steadily replaced with more minimally invasive endovascular techniques, and such minimally invasive advances in endovascular technology are altering the way surgeons treat vascular diseases.

While vascular surgical procedures are safer than ever, complex vascular surgical procedures can result in collateral damage to the patient. While no surgery is without risk, the level of skill of the surgeon and his/her team, as well as the ability to minimize unforeseen surprises when performing the surgical procedure, are paramount to preventing complications and/or death to the patient. Experienced surgeons, having performed numerous vascular disease procedures, are much more likely to complete such surgical procedures with fewer complications than those surgeons having less experience. While such experience is gained by training and performing numerous procedures, the number of surgical procedures available is a limiting factor. Accordingly, not every surgeon will have the same opportunity to perform the number of surgical procedures needed to obtain a skill level that minimizes the risks of the procedures undertaken. Moreover, as new procedures are developed, senior surgeons may find it difficult to obtain the necessary experience needed.

Training devices for practicing various surgical procedures have been used by surgeons to improve skills and are known in the art. For example, U.S. Pat. No. 8,016,598, U.S. Pat. No. 7,976,313, and U.S. Pat. No. 7,976,312 describe patient simulator systems for teaching patient care. U.S. Pat. No. 7,798,815 discloses an electromechanical pumping system for simulating the beating of a heart in a cardiac surgery training environment. U.S. Pat. No. 7,866,983 discloses a surgical simulator for teaching, practicing, and evaluating surgical techniques. The simulator is described as comprising a cassette of organs, blood vessels, and tissues that may be disposable.

U.S. Pat. No. 7,083,418 discloses a model for teaching or illustrating surgical and/or medical techniques. The system is described as having a base component representing tissue or an organ, and several components structured and arranged to be coupleable to and detachable from the base component and/or to each other, to illustrate different positions of the components with respect to one another, representing different phases in surgical and/or medical techniques.

U.S. Pat. No. 7,063,942 discloses a system for hemodynamic simulation. The system is described as comprising a vessel having properties of a blood vessel, a reservoir containing a quantity of fluid, tubing connecting the vessel and reservoir, and at least one pump for circulating the fluid within the system.

U.S. Pat. No. 6,843,145 discloses a cardiac phantom for simulating a dynamic cardiac ventricle. The phantom is described as comprising two concentrically-disposed, fluid-tight, flexible membranes defining a closed space between the walls of the membranes.

U.S. Pat. No. 6,685,481 discloses a training device for cardiac surgery and other similar procedures. The device is described as including an organ model such as a cardiac model, an animation network adapted to impart to the model a motion similar to the corresponding natural organ, and a control device used to control the operation of the animation network. The cardiac model is described as being made of two sections, an inner cast simulating the myocardium and an external shell simulating the pericardium.

U.S. Pat. No. 5,052,934 discloses an apparatus to serve as a phantom for evaluation of prosthetic valves and cardiac ultrasound procedures, wherein a controlled pulsatile flow of a blood-mimicking fluid is passed through a multi-chambered region into which are mounted mitral and aortic valves and adjustably positionable ultrasound transducers.

While such training devices are known in the art, the device and system for simulating normal and disease state cardiovasculature functioning in accordance with the present invention provides a training tool that is more physiologically correct than such prior art devices, and provides automatic adjustment of one or more functioning elements, i.e. resistance valves or compliance chambers, to provide more accurate and representative pressure and fluid flow profiles, thereby providing a mechanism to reduce collateral damage associated with cardiovasculature procedures.

SUMMARY OF THE INVENTION

The present invention describes a device and system for simulating normal and disease state cardiac and vascular functioning, including anatomically accurate elements, i.e. cardiac (heart) and vasculature (blood vessels), for training and medical device testing. The system and device uses pneumatically pressurized chambers to generate ventricle and atrium contractions. While actuation is described throughout the specification as being pneumatically driven via pressurized air, actuation may also be accomplished via other mechanisms, such as the use of pressurized liquids, or the combination of pressurized air and pressurized liquid. In conjunction with the interaction of synthetic or natural mitral and aortic valves, the system is designed to generate pumping action that produces more accurate volume fractions, and pressure gradients of pulsatile flow, duplicating that of a human heart. The present system further uses one or more sensors or meters to monitor and/or change one or more characteristics of the system. For example, various sensors are used to control or provide proper representations of systolic and/or diastolic pressures as desired. Flow meters for determining and/or modifying flow rates throughout the system may be utilized as well. As such, one or more feedback loops are used to adjust such characteristics, thereby allowing for a more accurate representation of the circulatory system. One or more control units or components are provided for controlling the overall functioning of the system. By providing a control unit that automatically changes one or more functioning components of the system, pressure and flow profiles can be generated without the need of manual adjustment.

The cardiovasculature training and evaluation simulator system and device suitable for training and testing medical devices is adapted to provide an anatomically and physiologically accurate representation of a cardiovasculature system in normal or diseased states. In an illustrative embodiment, the system comprises a pneumatically driven cardiac module for simulating cardiac functioning of a patient, a vasculature system module fluidly connected to the cardiac module and adapted for simulating the vasculature of a patient, and a control component operatively coupled to the cardiac module and the vasculature system module. A control unit is configured to control or modify one or more operational parameters of the system, including heart rate, ejection fraction, systemic vascular resistance and compliance. By modifying the system parameters, pathological hemodynamic states, including but not limited to sepsis, hyperdynamic therapy with vasopressor agents, or cardiac arrhythmias, such as atrial fibrillation or flutter can be recreated. The system may also contain replication of other body components, preferably the cerebrovasculature.

The system and devices, therefore, provide a mechanism that can be used to reduce collateral damage to patients undergoing vascular surgeries resulting from surgeon inexperience or inexperience with complex procedures. By providing a device that replicates the heart and vasculature, the surgeon can perform endovascular procedures prior to having to perform such procedures on the actual patient. Device selection, placement, and optimization can be determined prior to actual surgery, eliminating the risk associated with having to do such tasks during a live procedure.

Accordingly, it is a primary objective of the invention to provide a device and system for simulating normal and disease state cardiovascular functioning.

It is a further objective of the invention to provide a device and system for simulating normal and disease state cardiovascular functioning including an anatomically accurate cardiac simulator for training and medical device testing.

It is yet another objective of the invention to provide a device and system for simulating normal and disease state cardiovascular functioning designed to generate pumping action that produces accurate volume fractions, duplicating that of a heart.

It is a further objective of the invention to provide a device and system for simulating normal and disease state cardiovascular functioning designed to provide pressure gradients of pulsatile flow that duplicates that of a heart and/or vascular elements.

It is yet another objective of the invention to provide a device and system for simulating normal and disease state cardiovascular function which controls air pressure level, fluid pressure, and heart rate, thereby inducing contractions that simulate a wide variety of heart conditions.

It is a still further objective of the invention to provide a device and system for simulating normal cardiovascular functioning which controls air pressure level, fluid pressure, and heart rate to induce contractions that simulate a wide variety of heart conditions having normal heart functions.

It is a further objective of the invention to provide a device and system for simulating disease state cardiovascular functioning which controls air pressure level, fluid pressure, and heart rate to induce contractions that simulate a wide variety of diseased or injured heart conditions.

It is a further objective of the invention to provide a training and evaluation simulator system and device suitable for training and testing medical devices which is adapted to provide an anatomically and physiologically accurate representation of a cardiovasculature system in normal or diseased states.

It is yet another objective of the invention to provide a training and evaluation simulator system and device having a control module adapted for controlling or modifying one or more operational parameters of the system, including heart rate, ejection fraction, systemic vascular resistance and compliance.

It is a still further objective of the invention to provide a training and evaluation simulator system and device in which pathological hemodynamic states, including but not limited to sepsis, hyperdynamic therapy with vasopressor agents, or cardiac arrhythmias, such as atrial fibrillation or flutter, including induced cardiac rapid pacing, can be recreated.

It is a further objective of the invention to provide a training and evaluation simulator system and device which allows a surgeon to perform endovascular procedures prior to having to perform such procedures on the actual patient.

It is yet another objective of the invention to provide a training and evaluation simulator system and device which allows a surgeon to determine device selection, placement, and optimization prior to actual surgery, eliminating the risk associated with having to do so during a live procedure.

It is a further objective of the present invention to provide a device and system for simulating normal and disease state cardiovascular function which utilizes feedback control mechanisms to achieve physiological representative biological profiles.

It is a further objective of the invention to provide a device and system for simulating normal and disease state cardiovascular function which utilizes systems to automatically adjust fluidic elements to achieve physiological representative biological profiles.

It is a further objective of the invention to provide a device and system for simulating normal and disease state cardiovascular function which utilizes systems to automatically control flow of fluid via pumping mechanisms to achieve physiological representative biological profiles.

It is a further objective of the invention to provide a device and system for simulating normal and disease state cardiovascular function which utilizes feedback control and automatic adjustment of fluidic elements and pump control to achieve physiologically representative pressure and flow profiles.

Other objectives and advantages of this invention will become apparent from the following description, taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 23B is a perspective view of the hardware component module associated with the cardiovascular simulation system illustrated in FIG. 1C or FIG. 1D, with the assembly bracket removed;

DETAILED DESCRIPTION OF THE INVENTION

Figure 1A:
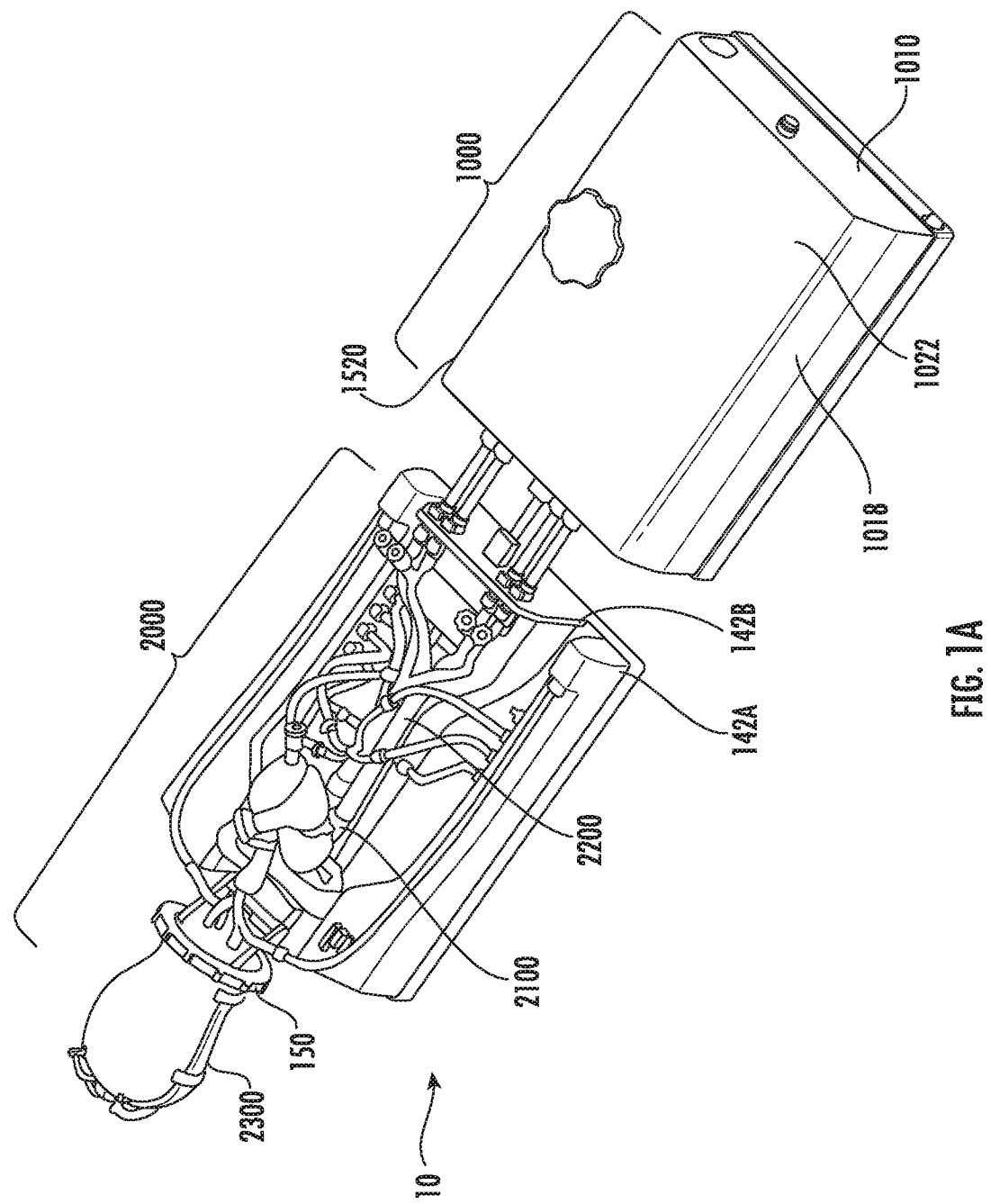
FIG. 1A is a perspective view of an embodiment of a cardiovascular simulation system.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1B:
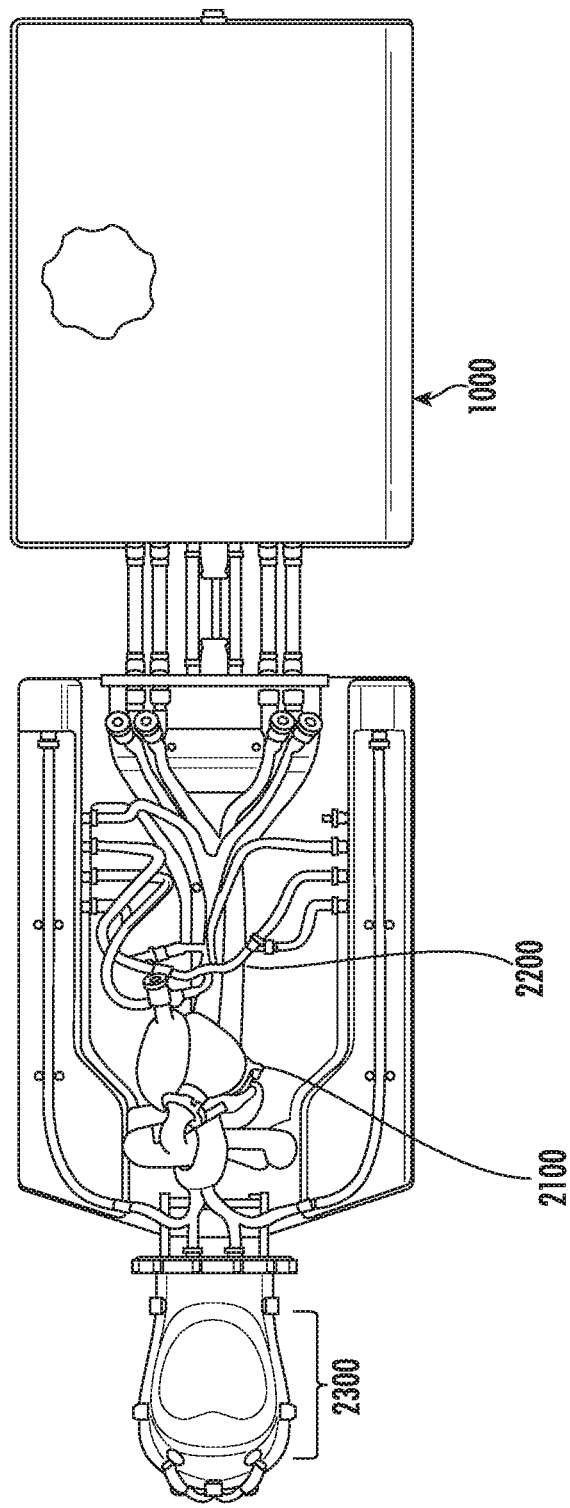
FIG. 1B is a top view of the cardiovascular simulation system illustrated in FIG. 1A.

Referring to FIGS. 1A and 1B, a simulation system or device, generally referred to as a cardiovascular simulation system 10, is illustrated. The cardiovascular simulation system is illustrated and described as a cardiovascular system. However, the simulator system is not limited to the cardiovascular system, and can be adapted to replicate other systems. The cardiovascular simulation system 10 comprises one or more modules, including a hardware component module and an anatomical component module. The hardware component module and the anatomical component module interact in a manner to provide a system which is an improved anatomically and functionally accurate replication of a body system, i.e. a cardiac and/or vasculature system. Providing such an improved anatomically correct system provides the user a unique tool to practice and train for various surgical procedures and/or techniques prior to having to perform such actions on a living system. While such system will be described using human anatomy and systems, the cardiovascular simulation system 10 in accordance with the instant invention can be adapted to replicate or model other organism systems, such as other mammals, including domesticated animals such as dogs or cats, rodents such as mice or rats, livestock such as cattle, horses, sheep, swine/porcine, or wild animals such as lions or tigers.

Both the hardware component module, referred to generally as 1000, and the anatomical module, referred to generally as 2000, further contain sub-modules. The sub-modules comprise individual components that drive the system and/or provide accurate structural and functional replication of a living system. As will be described in greater detail, the hardware component module 1000 contains one or more sub-modules, including a pneumatics component, a hydraulics component, and a control/electronics component. The cardiovascular simulation system 10 is designed to include one or more feedback loops configured to provide accurate and automatic representation of several important components or characteristics of the system, i.e. physiologically representative operation of the cardiovasculature and cerebrovasculature, including flow rate and valve operations. The control unit contains the necessary hardware and monitoring devices to provide automatic manipulation of the system to provide predetermined characteristics of blood flow or pressure. The control unit may include pressure sensors to represent arterial and venous pressure, and/or flow sensors to represent cephalic, thoracic, and visceral flow in order to monitor and provide physiological values of pressure and flow within the system. Information obtained from the pressure and flow sensors are used as part of feedback control mechanisms to achieve physiologically representative characteristics. One or more valves may also be used to provide control of fluid flow in the system. The anatomical module 2000, illustrated herein as a cardiovasculature system, is primarily made up of three sub-modules, including a cardiac simulator module 2100, a vasculature simulator module 2200, and one or more peripheral organ/systems simulator module 2300. The cardiovascular simulation system 10 may be designed so one or more individual parts or components that make up the cardiac simulator module 2100, a vasculature simulator module 2200, and one or more peripheral organ/systems simulator module 2300 can be replaced by replacement parts or components. In this configuration, one or more parts or components of each module may be disassembled, replaced, and reassembled with the new parts or components.

The cardiovascular simulation system 10 may include a support structure 142A or 142B, see FIG. 1A, which may be used to support the various components of the cardiovascular simulation system 10. Each of the components may be secured to the support structure using, for example, screws, nuts and bolts, or may be secured using chemical fastening, such as an adhesive. The cardiovascular simulation system 10 comprises one or more modules, including a hardware component module and an anatomical component module. The hardware component module and the anatomical component module interact in a manner to provide a system which is an improved anatomically and functionally accurate replication of a body system, i.e. a cardiac and/or vasculature system.

The cardiac simulator module 2100 includes a replica of the human heart, including all four chambers, the left and right atrium and the left and right ventricles, and cardiac valves, including the mitral and aortic valves and the pulmonary and tricuspid valves. Functioning of several components of the cardiac simulator module 2100 are driven by air pressure.

Figure 1C:
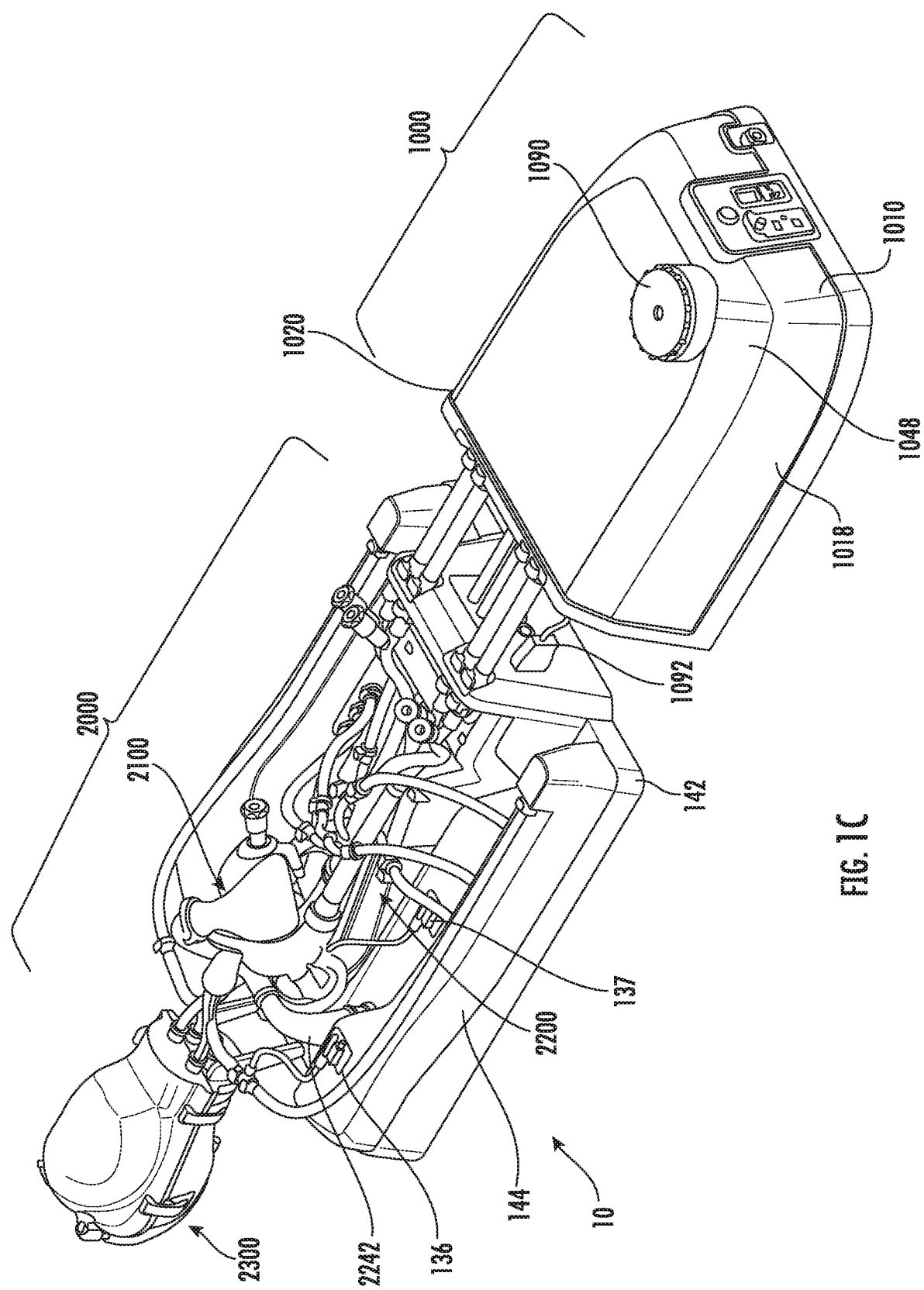
FIG. 1C is a perspective view of an alternative embodiment of the cardiovascular simulation system.
Figure 1D:
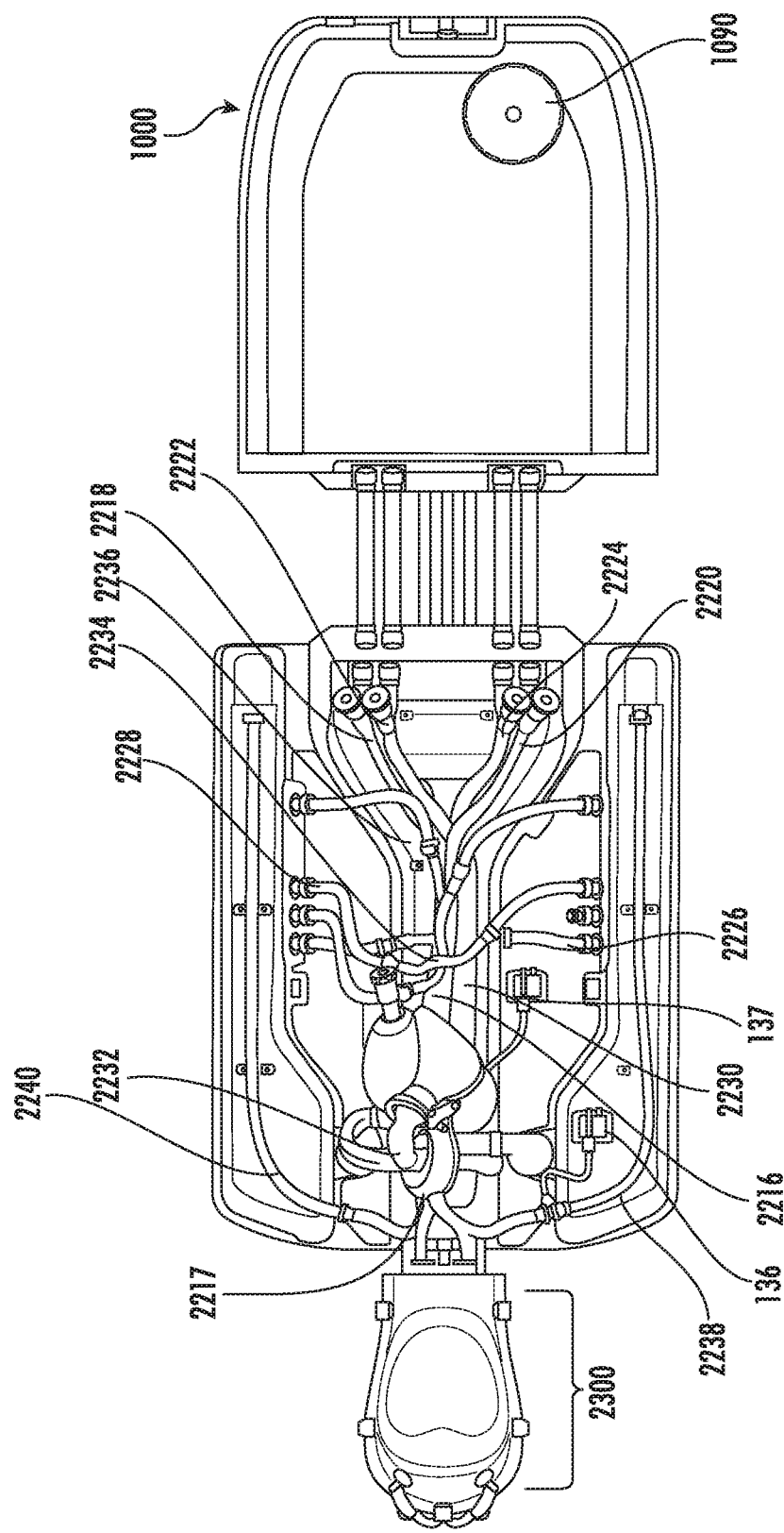
FIG. 1D is a top view of the cardiovascular simulation system illustrated in FIG. 1C.
Figure 2:
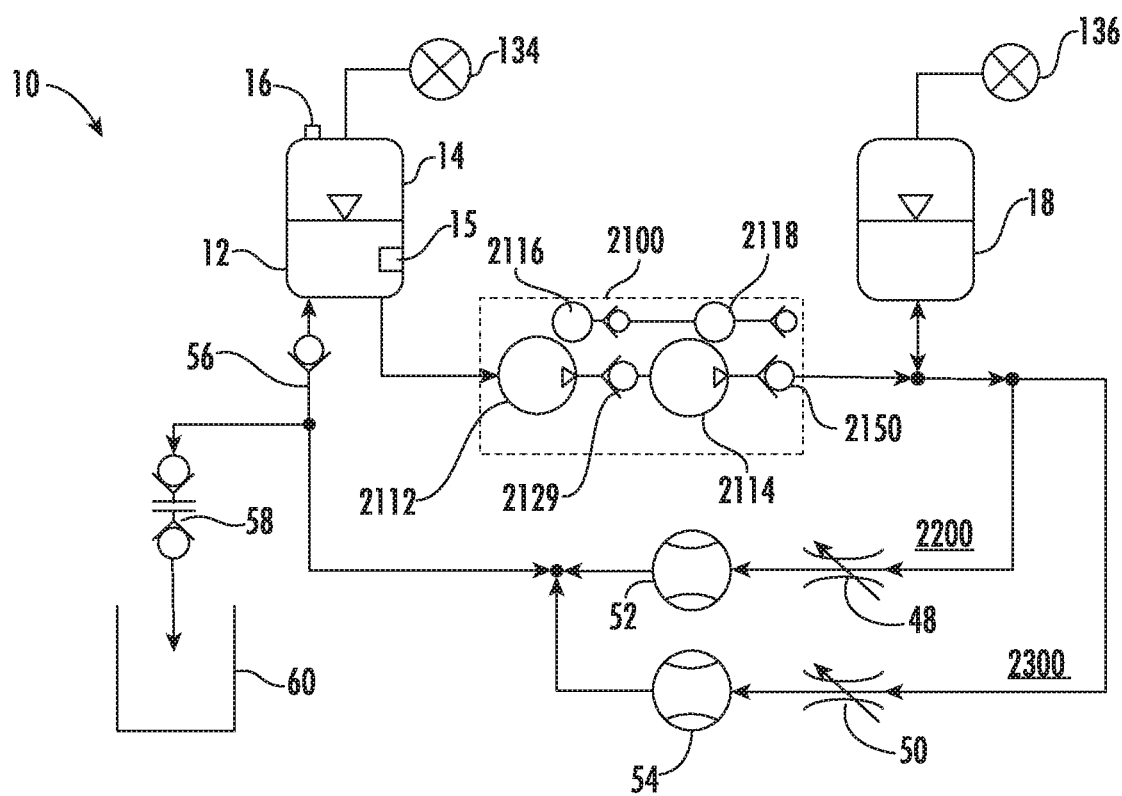
FIG. 2 is a block diagram of the general hydraulic circuit schematic associated with the simulator system in accordance with an illustrative example of the present invention.

FIGS. 1C and 1D illustrate an embodiment of the cardiovascular simulation system 10 having several additional features or components and many of the same features or components as that described in FIGS. 1A and 1B. As such, any features described herein, including the later described pneumatic, hydraulic, or electrical schematics, unless noted to the contrary, may be applicable to the cardiovascular simulation systems 10 shown in FIG. 1A, FIG. 1B, FIG. 1C, or FIG. 1D, in any combination, even if not specifically illustrated. The cardiovascular simulation system 10 may include a support structure 142, which may be used to support the various components of the cardiovascular simulation system 10. The cardiovascular simulation system comprises the hardware component module, referred to generally as 1000, and the anatomical module, referred to generally as 2000. The anatomical module 2000, illustrated herein as a cardiovasculature system, is primarily made up of three sub-modules, including a cardiac simulator module 2100, a vasculature simulator module 2200, and one or more peripheral organ/systems simulator module 2300. FIG. 1C illustrates several tubing representing several (not all) components of the vasculature simulator module 2200, including descending aorta 2216, ascending aorta 2217, left/right iliac arteries 2218, 2220, left/right iliac veins, 2222, 2224, renal arteries 2226, 2228, inferior vena cava 2230, pulmonary artery trunk 2232, and visceral arteries (i.e. Celiac, Superior Mesentery, Inferior Mesentery) 2234, 2236. The vasculature simulator module 2200 may also include the arm vasculature, 2238, 2240. A conical shaped (or any shape having a smaller diameter at the aorta and then getting larger as needed away from the aorta) compliance tap 2242 to the arterial compliance chamber 18 may be used in order to reduce the hydraulic inertence of this fluid connection. Sensors 136 and 137 are also illustrated.

FIGS. 2-4B provide block diagrams illustrating the general hydraulic circuit schematics, pneumatic circuit schematics, and electronic circuitry schematics of the cardiovascular simulation system 10. As illustrated in FIGS. 2-4B, the cardiovascular simulation system 10 is a closed loop system designed to replicate the closed loop circulatory system of a human or other animal. The cardiovascular simulation system 10 includes a fluid reservoir (also known as a venous chamber) 12, which is fluidly connected to a first portion of the anatomical module 2000, and a cardiac simulator module 2100. The fluid reservoir or venous chamber 12 comprises a housing unit 14 which is sized and shaped to receive and hold a fluid. Within the housing unit 14, the fluid reservoir or venous chamber 12 may contain one or more heating mechanisms 15, such as heating coils that allow for the fluid within the cardiovascular simulation system 10 to be warmed to a predetermined temperature which corresponds to the physiological fluid temperatures within a body. The fluid may be any liquid that simulates blood. In an illustrative embodiment, the fluid is a clear blood analog having properties which duplicate the viscosity of human blood and mimics the friction coefficients as endovascular devices, wires, and catheters traverse the vasculature system. Alternatively, the fluid can be whole blood, or may simply utilize water. Accordingly, any fluid can be used and modified to have the viscosity and/or flow rate that is the same as or approximates that of blood flow through veins or arteries. The fluid could be clear, or may include a dye so that the fluid flow can be visualized throughout the system. A fill cap 16 is used to add a fluid, such as water, to the cardiovascular simulation system 10. The fluid reservoir or venous chamber 12 can be sealed and pressurized to provide a baseline pressure, replicating the venous pressure, to affect passive filling of the cardiac simulator module 2100. Alternatively, fluid may be drawn into the system through other means. The cardiovascular simulation system 10 illustrated in FIG. 1C and FIG. 1D may include a centrifugal pump, to be described later. The centrifugal pump may be used to actively fill/prime the cardiovascular simulation system 10 instead of the need for pressurizing the fluid reservoir or venous chamber 12. If used, the centrifugal pump may be controlled by a pressure sensor 137. The centrifugal pump may be throttled based on the pressure read at that sensor to maintain venous pressure at a predetermined value, such as 10-20 mmHg. The top fluid reservoir or venous chamber 12 may contain indicators, such as a gauge (not illustrated), or a window may be utilized to provide visual confirmation of flow level. Alternatively, a sensor may be used and coupled to the control unit to provide indications of high, low, or appropriate fluid levels.

The cardiovascular simulation system 10 is designed to replicate the blood flow from the heart, particularly the left side of the heart, out to other parts of the body. As such, the cardiac simulator module 2100 could include pumps or air compressors which are designed to push fluid out of the module and into other components of the cardiovascular simulation system 10, thereby replicating the flow of blood through the chambers of the heart, preferably the left atrium and the left ventricle, but also through the right atrium and right ventricle, if required. An embodiment of the cardiac simulator module 2100, which includes replicas of the anatomy of the heart, is shown in FIGS. 6-9. As illustrated in the figures, the cardiac simulator module 2100 comprises a heart module 2110 having four chambers, representing the anatomy of the left and right sides of the heart, including the left atrium 2112, the left ventricle 2114, the right atrium 2116, and the right ventricle 2118. The heart module 2110, including the individual chambers representing the left and right atriums and the left and right ventricles, may be molded using a standard size and shape. To allow fluid flow into the left ventricle at the appropriate time, i.e. when the left atrium contracts, without fluid flowing back into the left atrium upon relaxation, the left atrium 2112 contains a one-way valve, illustrated herein as a synthetic valve 2129, see FIG. 9. The valve 2129 represents a mitral valve and, as an illustrative example, could be a synthetic replication. Alternatively, the valve 2129 may be a transplant of an actual mammalian mitral valve, such as a swine or a human mitral valve. To allow fluid flow into the right ventricle at the appropriate time, i.e. when the right atrium contracts, without fluid flowing back into the right atrium upon relaxation, the right atrium 2116 contains a one-way valve, illustrated herein as a synthetic valve 2131, see FIG. 9. The valve 2131 represents a tricuspid valve and, as an illustrative example, could be a synthetic replication. Alternatively, the valve may be a transplant of an actual mammalian tricuspid valve, such as a swine or a human tricuspid valve. The heart module 2110 may also contain additional valves, representing an aortic valve or a pulmonic valve (not shown).

Preferably, the present invention uses a heart module 2110 in which the atriums and ventricles have been molded using Computer Tomography (CT Scan) imagery of a heart, as well as its vasculature. The left atrium 2112, the left ventricle 2114, the right atrium 2116, the right ventricle 2118, or combinations thereof, can be molded to represent the exact size and shape analogous to that of individual patients. The figures illustrating the heart module 2110 do not include any vasculature. However, any of the components described herein forming the heart module 2110 may be adapted to include anatomically correct vasculature, such as the left coronary artery, the left circumflex artery, the left marginal artery, the left anterior descending artery, and the diagonal branch of the left ventricle chamber. The vasculature can be "normal" vasculature, or can be that of disease state vasculature. In addition, the normal or the disease state vasculature can be adapted to represent the exact vasculature of individual patients (through use of CT scans, MRI and/or rotational angiography), or can be designed to represent normal/disease states not associated with a specific patient. Moreover, sections of any of the components described herein forming the heart module 2110 may also include thick sections (simulating ventricular hypertrophy) and/or thinner sections (simulating ventricular hypotrophy) to simulate differing resistance of the heart to contraction and expansion.

Figure 5:
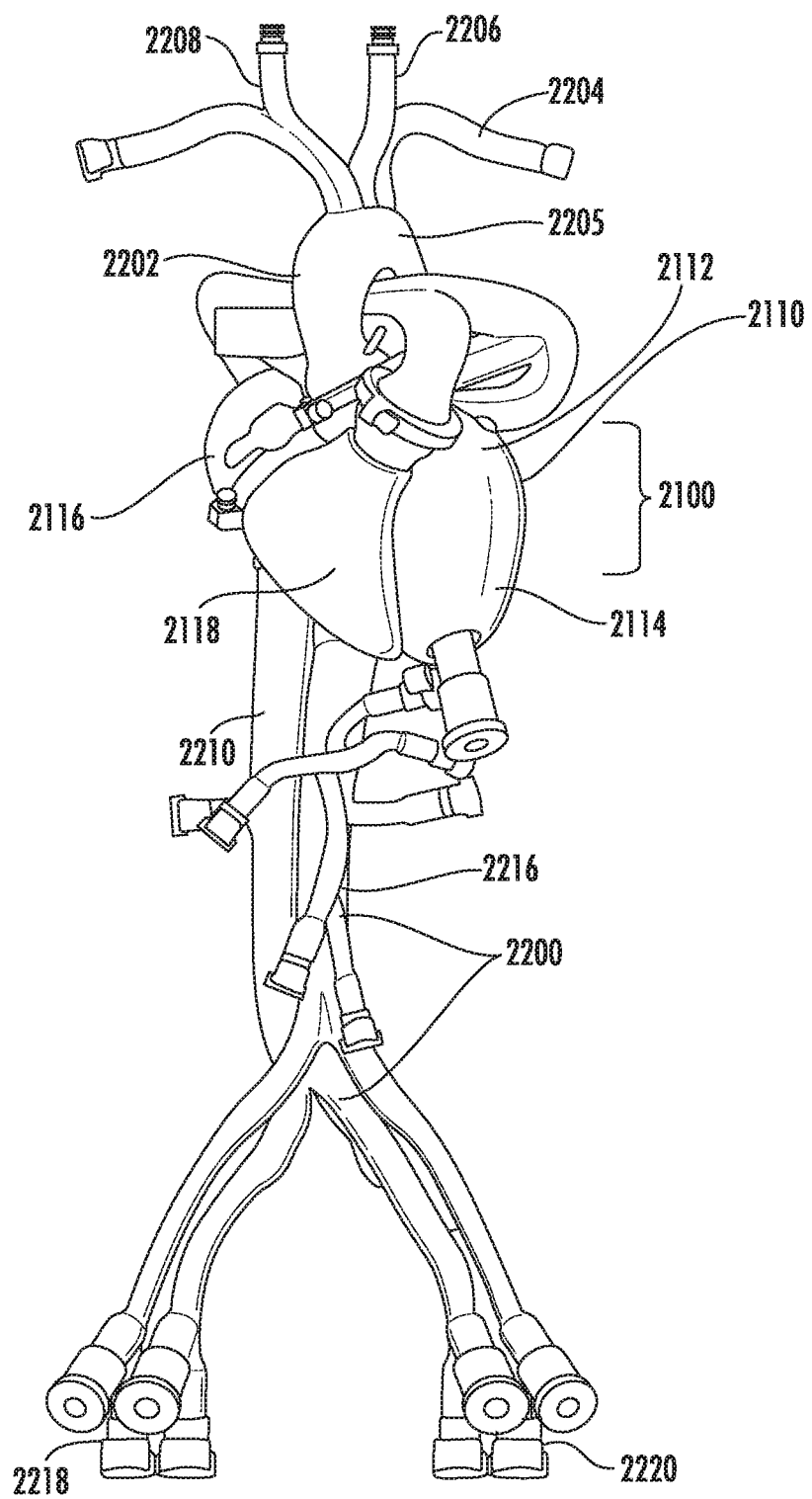
FIG. 5 is a partial perspective view of the cardiac simulator module and ventricular module.
Figure 6:
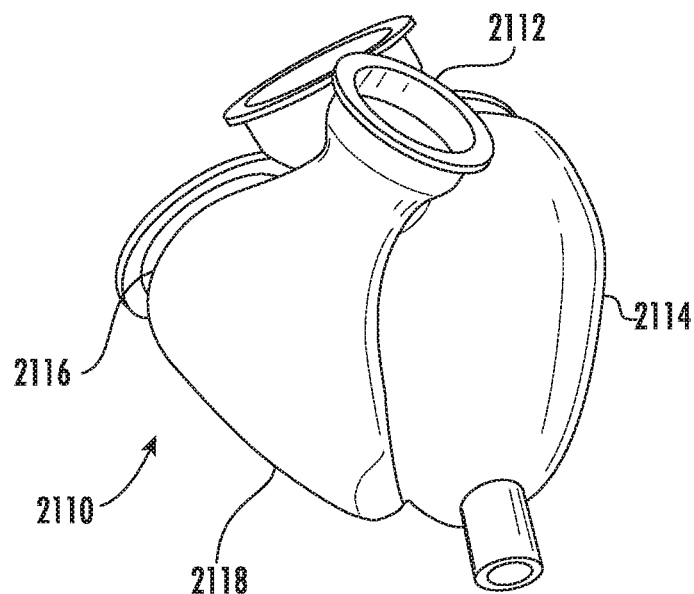
FIG. 6 is a perspective view of the heart module.
Figure 7:
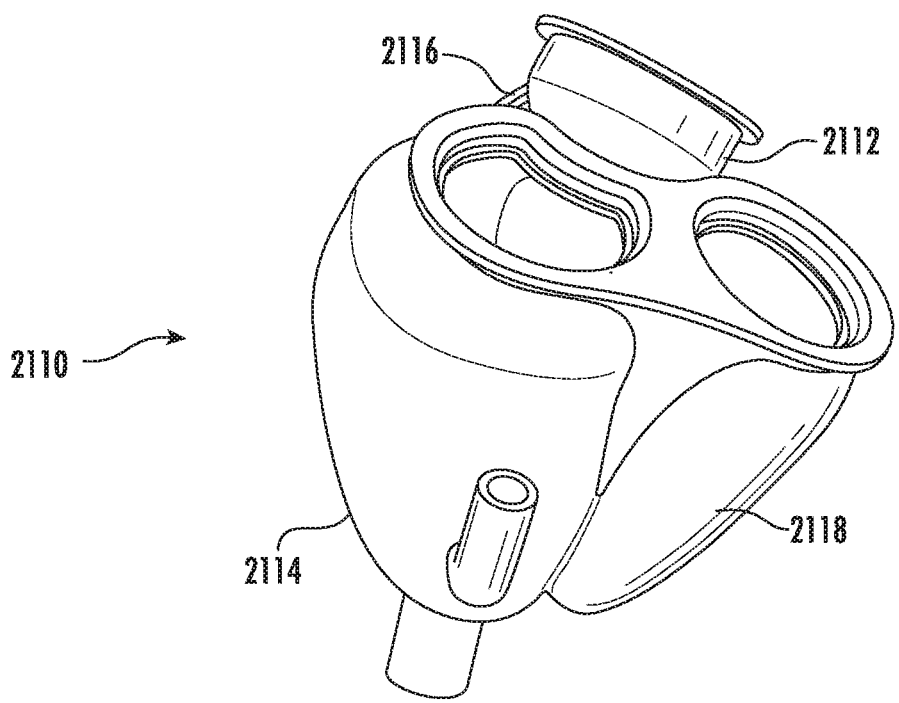
FIG. 7 is an alternative perspective view of the heart module.
Figure 8:
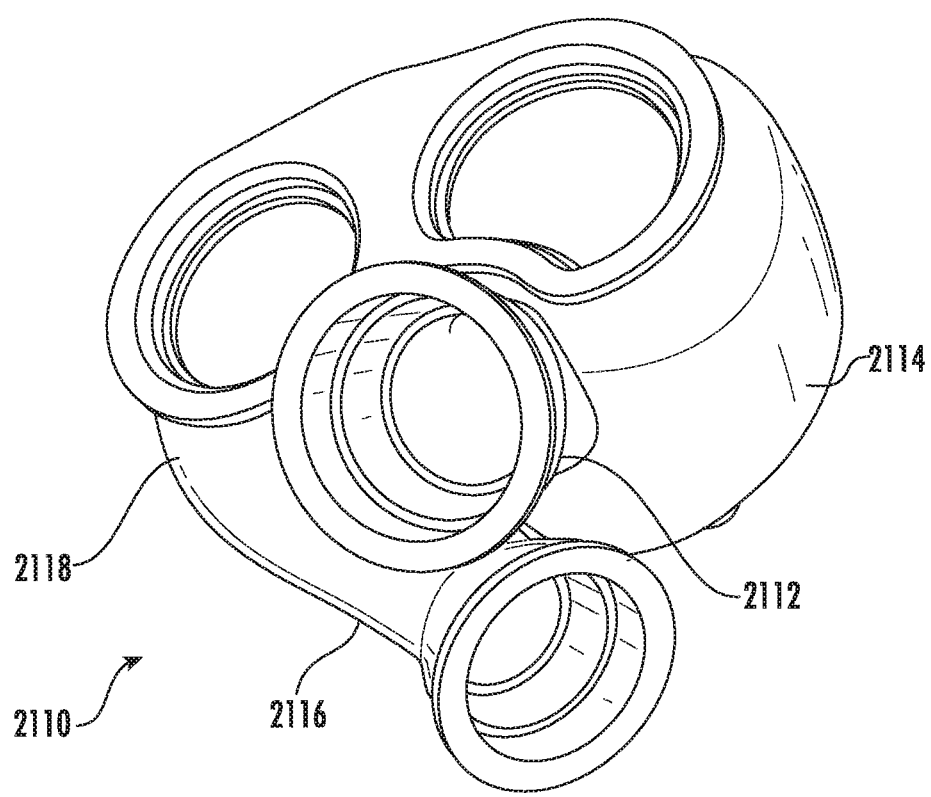
FIG. 8 is an alternative perspective view of the heart module.

FIG. 5 also illustrates the vasculature simulator module 2200, representing the various veins or arteries associated with blood flow in a mammal. The vasculature module simulator 2200 is made of a plurality of members, such as synthetic tubing, that provide fluid flow into and away from the cardiac simulator module 2100. Similar to the atrium and ventricle of the cardiac simulator module 2100, the vasculature simulator module 2200 tubing can be made to replicate the size, shape, and tonometry of the vasculature of specific patients. Preferably, the tubing is made of clear medical grade plastics having flexural modules, or stiffness, which corresponds to a desired need. Referring to FIG. 5, fluid flows out of the left ventricle chamber 2114 and into tubing representing the aorta 2202 and aortic arch 2205. One or more aorta connectors, such as but not limited to, 2204 (subclavian artery), 2206 (common carotid artery), and 2208 (brachiocephalic artery), are used to fluidly attach to other components of the vasculature simulator module 2200, such as tubing representing the vertebral arteries 2310, and fluidly connect to the periphery organ/system module 2300 (see FIG. 1A, 1B, 1C, 1D or FIG. 2) using tubing that represents the left common carotid artery and the right common carotid artery. Fluid further flows into the descending aorta 2216 and connects to tubing representing the right iliac artery 2218 and the left iliac artery 2220. Fluid flow out of the cardiac simulator module 2100 is directed through additional tubing, depending on which part of the system the fluid is traveling through.

Figure 3:
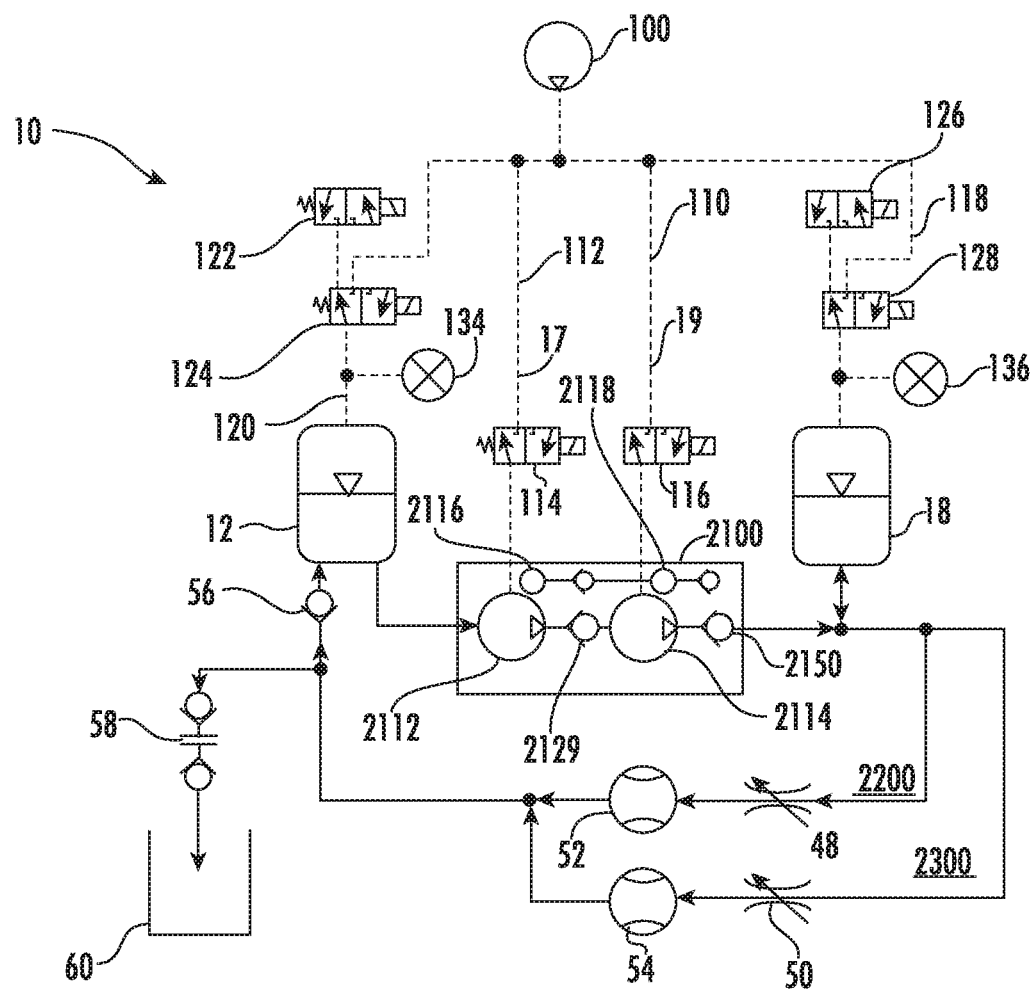
FIG. 3 is a block diagram, as shown in FIG. 2, including the general pneumatic circuit schematic associated with the simulator system in accordance with an illustrative example of the present invention.

The cardiac simulator module 2100, preferably the left atrium 2112 or left ventricle 2114, pneumatically connects to the pneumatics module 100, illustrated as a compressor, through tubing 17 and 19 (see FIG. 3). The pneumatics module 100 contains the necessary components to provide one or more modules of the cardiovascular simulation system 10 with compressed air. The compressed air generated allows one or more of the components of the cardiac simulator module 2100, which is pneumatically connected to the compressor 100, to compress and forcibly expel any substance, such as liquid contained therein, out, as will be described later. Accordingly, the air compressor acts to provide the cardiac simulator module 2100 with accurate simulation of cardio dynamic functions. Alternatively, compressed air may be provided by one or more pumps. Injection ports may be included to provide a mechanism to inject dyes or representative medicine into various places within the cardiovascular simulation system 10.

Figure 9:
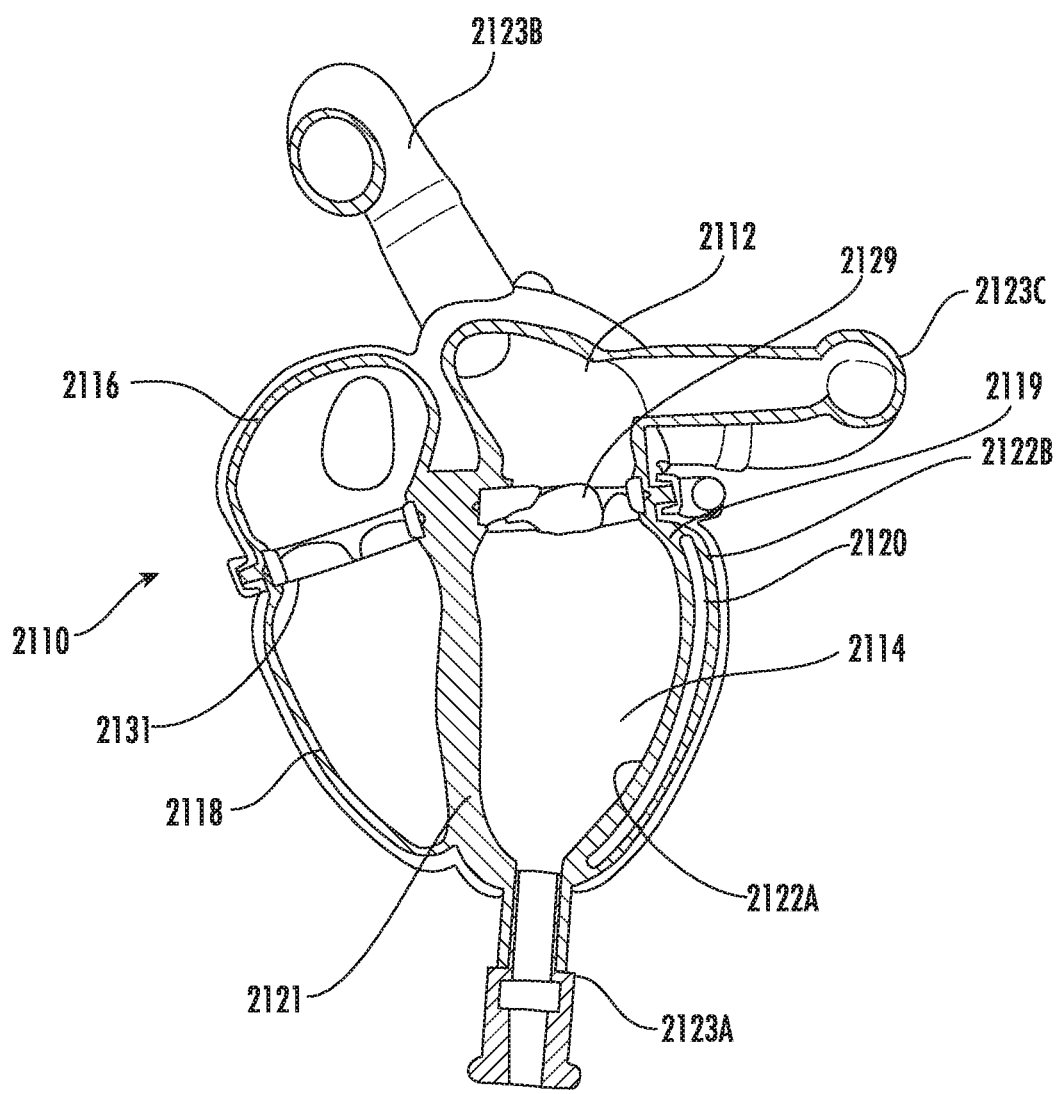
FIG. 9 is a cross sectional view of the heart module, illustrating the left ventricle cavity.
Figure 10:
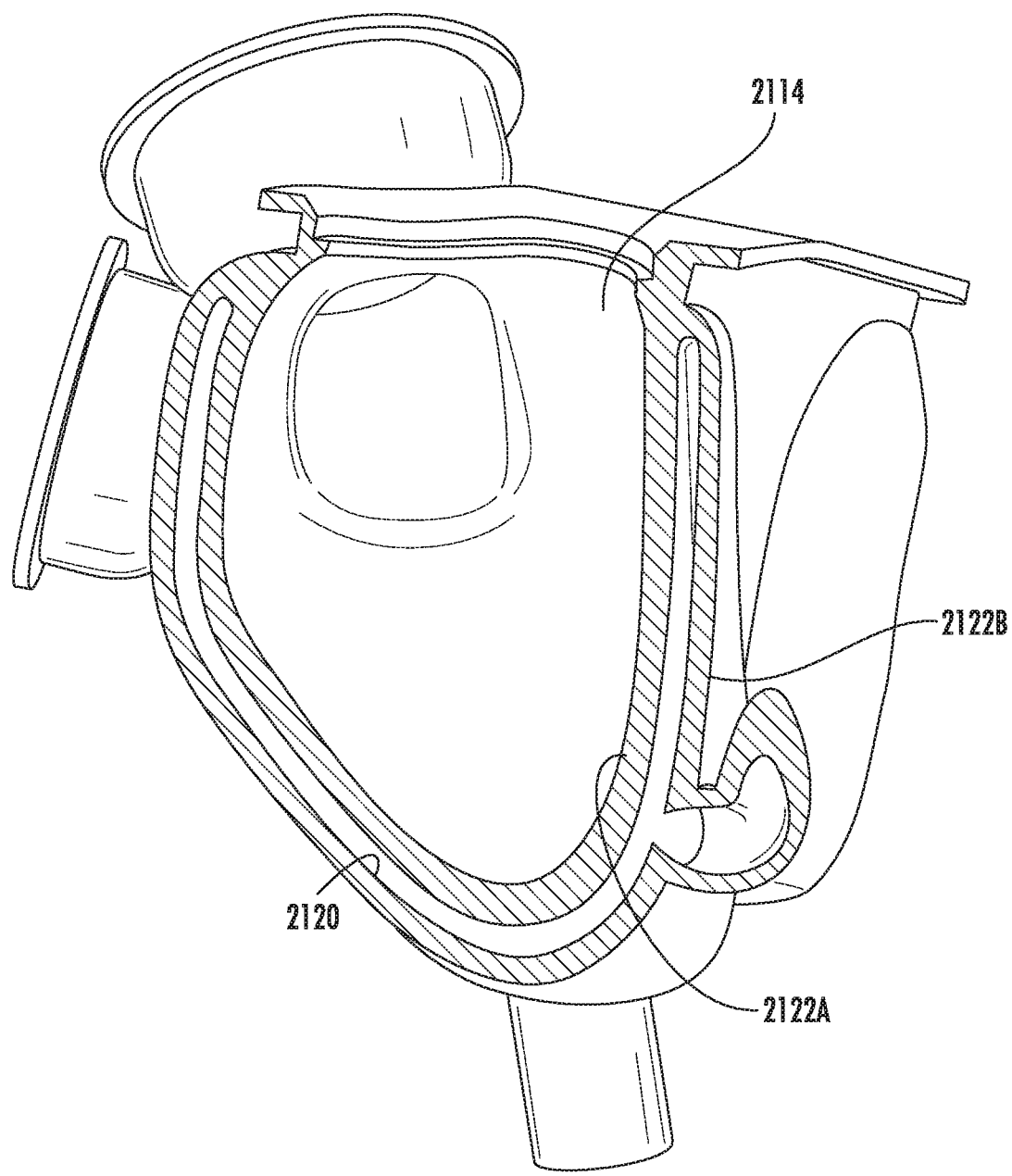
FIG. 10 is a cross sectional view of the left ventricle of the heart module.
Figure 11:
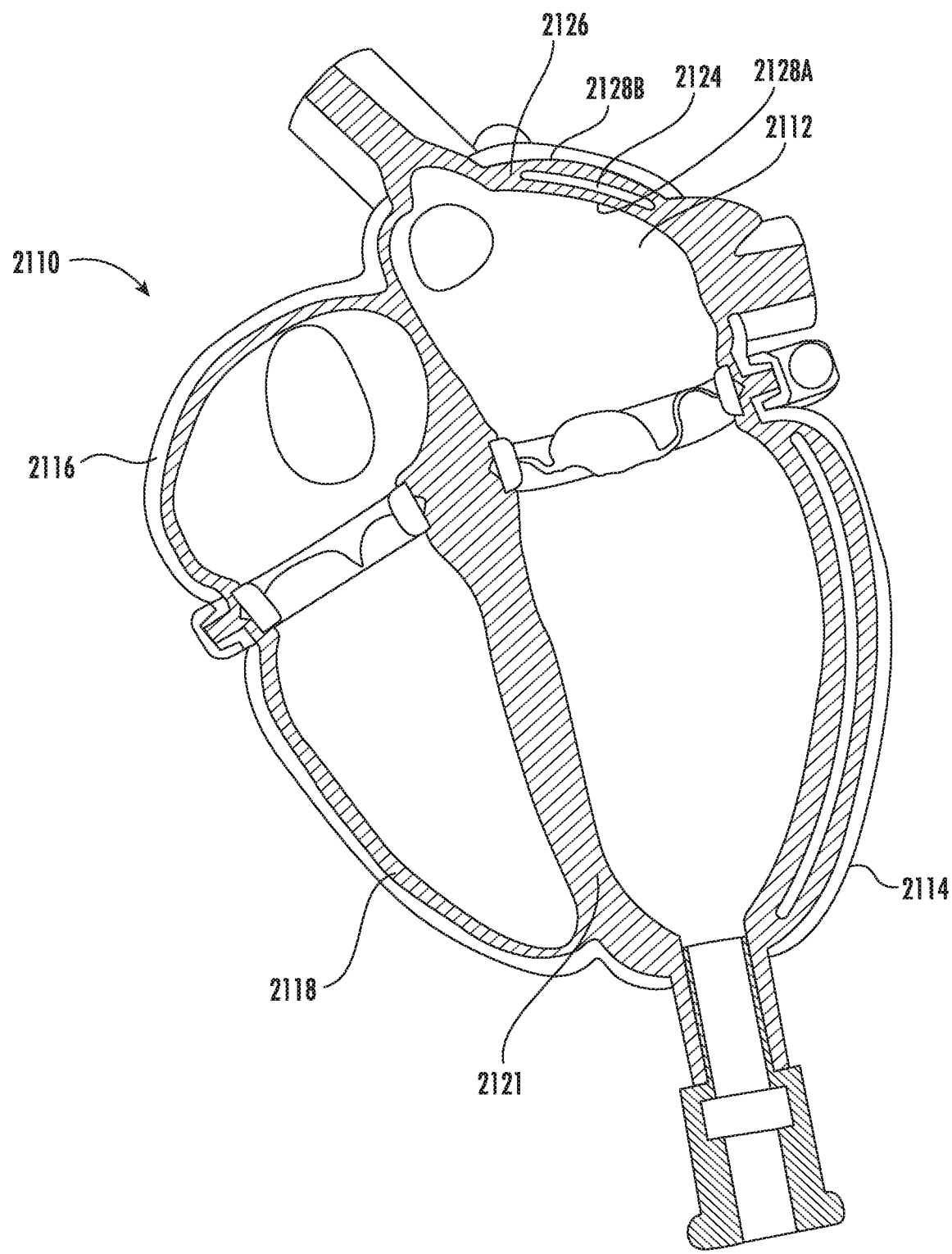
FIG. 11 is a cross sectional view of the heart module, illustrating the left atrium and ventricle cavities.
Figure 12:
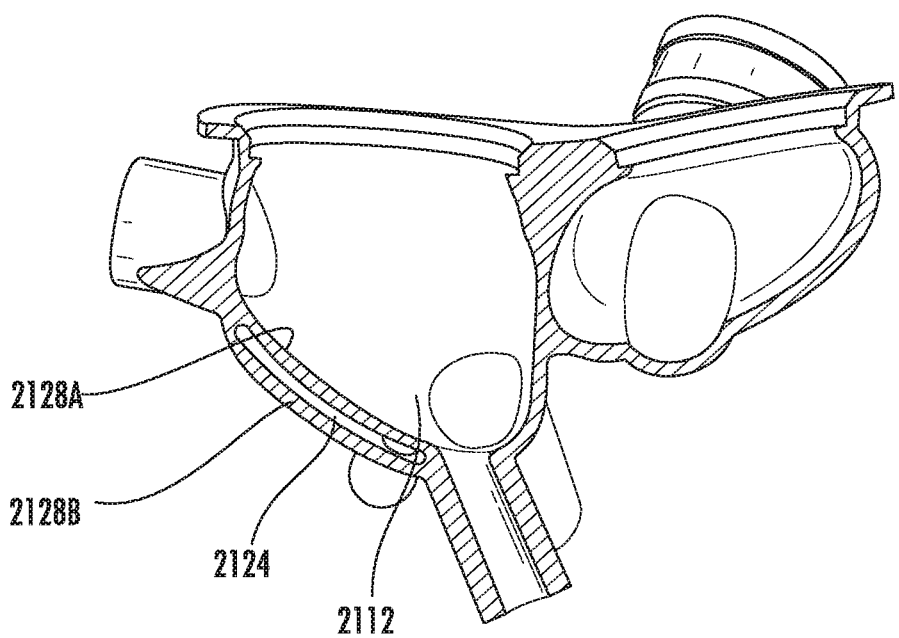
FIG. 12 is a cross sectional view of the heart module, illustrating the cavity of the left atrium.

The heart module 2110 is preferably made of a soft plastic material, such as silicone. Each chamber, the left atrium 2112, the left ventricle 2114, the right atrium 2116, or the right ventricle 2118, is made with a cavity molded within the elastic membrane wall, thus providing a mechanism for pneumatic pressurization. If not used as part of the cardiac module functioning, the right atrium 2116, the right ventricle 2218, or both may be included as part of the heart module 2110, but not have the cavity molded within the elastic membrane wall. Referring to FIGS. 9 and 10, the cross-sectional view of the heart module 2110 illustrates the left ventricle 2114 with a left ventricle cavity 2120 separating the left ventricle membrane wall 2119 into an inner left ventricle membrane wall 2122A and an outer left ventricle membrane wall 2122B, see FIG. 10. The inner left ventricle membrane wall 2122A has a desired strength to prevent extending outwardly and collapsing the left ventricle cavity 2120 when a fluid is placed within the left ventricle chamber 2114, but will collapse inwardly when pressurized air is forced within the left ventricle cavity 2120, thus pushing fluid out of the left ventricle chamber 2114. Preferably, the left ventricle cavity 2120 extends around the entire perimeter of the left ventricle chamber 2114. FIG. 11 is a cross sectional view of the heart module 2110 showing the left atrium 2112 with the left atrium cavity 2124 within the left atrium membrane wall 2126. The left atrium cavity 2124 separates the left atrium membrane wall 2126 into an inner left atrium membrane wall 2128A and an outer left atrium membrane wall 2128B. Preferably, the left atrium cavity 2124 extends around the entire perimeter of the left atrium 2112, see FIG. 12. The inner left atrium membrane wall 2128A has a desired strength to prevent extending outwardly and collapsing the left atrium cavity 2124 when a fluid is placed within the left atrium chamber 2112, but will collapse inwardly when pressurized air is forced within the left atrium cavity 2124, thus pushing fluid out of the left atrium chamber 2112. Although not shown, the right atrium and ventricle may comprise the same cavity feature. While actuation of several components of the cardiovascular simulation system 10 is described as being pneumatically driven via pressurized air, actuation may also be accomplished via other mechanisms, such as the use of pressurized liquids, or combination of pressurized air and pressurized liquid.

The heart module 2110 can be pneumatically pressurized to actuate the left atrium 2112 and the left ventricle 2114. Pressurized air enters the left ventricle cavity 2120 or the left atrium cavity 2124, thus exerting a force on the respective inner membrane walls 2122A or 2128A. The force exerted by the pressurized air causes the respective inner membrane walls 2120A or 2128A to partially collapse or move inwardly, thus causing fluid stored within the left ventricle 2114 or left atrium 2112 to be pushed or expelled out.

Figure 13:
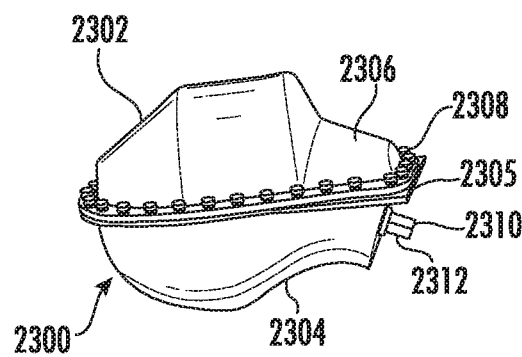
FIG. 13 is a perspective view of an illustrative example of the head module.
Figure 14:
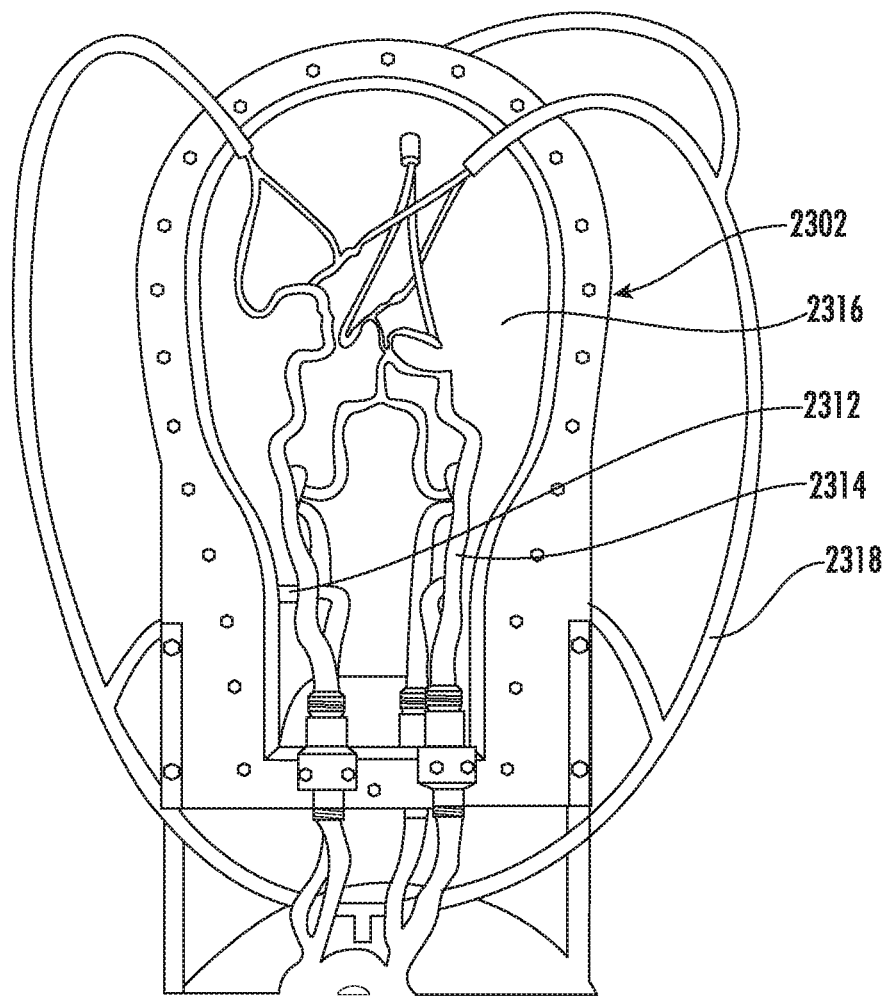
FIG. 14 is a perspective view of the head module shown in FIG. 13, shown with cerebrovasculature.

Referring to FIGS. 13 and 14, the periphery organ/system module 2300 is shown as a head module, or head 2302. The head 2302 contains a bottom portion 2304 connected to a board 2305 and/or a top portion 2306 through fastening members 2308, such as screws or nuts. Such arrangement allows for the top portion 2306 to be removed and replaced. The bottom portion 2304 contains one or more fluid connectors 2310 and 2312 which are adapted to fluidly connect the head 2302 to one or more components of the vasculature simulator module 2200. Such fluid connection allows the user to evaluate the effects of surgical techniques or procedures with peripheral organs or systems.

FIG. 14 shows an illustrative example of the head module 2302 with a plurality of tubing, 2312 and 2314, representing the cerebrovasculature. The cerebrovasculature is placed within a gel like material 2316 in order to mimic the compliance of the vessels in the subarachnoid space and surrounding brain. The vasculature system, from the carotid bifurcation to the intracranial circulation, as well as any pathology, can be replicated. The head module 2302 may also contain additional tubing 2318 connectable to other parts of the cardiovascular simulator system 10.

The cardiovascular simulator system 10 may use one or more compliance chamber modules. The compliance chamber modules act as system fluid storage devices and are adapted to functionally provide dynamic control over the systemic compliance depending on user required hemodynamics. Accordingly, the compliance chamber provides an anatomically correct range of cardiac system compliance and compensation, given that the cardiovascular simulator system 10 does not replicate all vasculature vessels contained within the entire human cardiovasculature system. For example, vasculature to the lower extremities, particularly the legs, is generally not included as part of the vasculature simulator module 2200. To replicate accurate cardio dynamics with anatomically accurate cardiac physiology while pumping into an incomplete modeled vascular system, the compliance chamber is used. The compliance chamber simulates the vascular volume and tonometry of the non-molded parts of the system. The vascular tonometry simulates arterial tension, and can be changed by adding or removing air from the compliance chamber. Depending on the amount of air, the conditions of hypertension or hypotension can be simulated.

Figure 17:
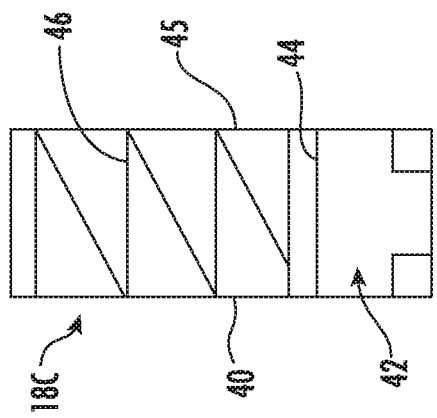
FIG. 17 illustrates a spring-loaded piston accumulator.
Figure 16:
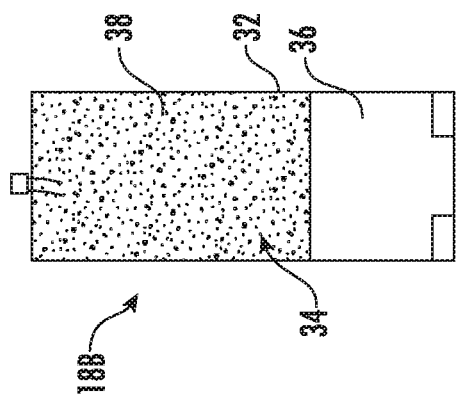
FIG. 16 illustrates a gas charged piston accumulator.
Figure 15:
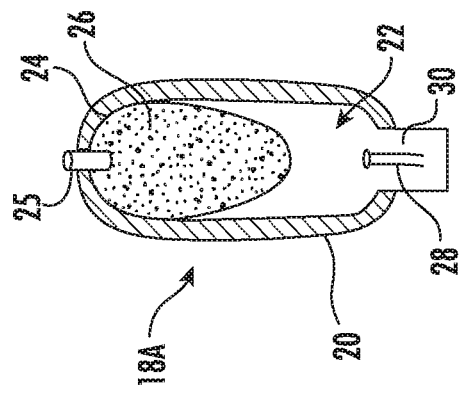
FIG. 15 illustrates a gas charged accumulator.

Referring to FIGS. 2-4B, the compliance module is illustrated as an accumulator, and referred to as the arterial compliance chamber 18. FIGS. 15-17 illustrate several embodiments of accumulators. FIG. 15 illustrates a gas charged accumulator 18A. Accumulator 18A comprises a housing unit 20 enclosing an internal cavity 22. Within the internal cavity 22 is a rubber bladder 24 for separating gas 26 (inserted through gas inlet 25) and any liquid stored within the internal cavity 22. A valve 28 may be placed within the discharge port 30. FIG. 16 illustrates a gas charged accumulator using a piston, referred to as 18B. The accumulator 18B also has a housing unit 32 having an internal cavity 34. A piston 36 separates the gas 38 and a liquid within the internal cavity 34. FIG. 17 illustrates a spring-loaded piston accumulator 18C. The spring-loaded piston accumulator 18C also contains a housing unit 40 having an internal cavity 42. A piston 44 with a spring 46 operates similar to the gas charged piston, except that the spring 46 forces the piston against stored liquid. Although not illustrated, alternative accumulator types, such as an accumulator that uses a diaphragm, known to one of skill in the art, may be used as well. The fluid reservoir 12 may be configured as an accumulator as well.

Referring back to FIG. 2, fluid from the cardiac simulator module 2100, directly, or if diverted to and returned from the arterial compliance chamber 18, is directed towards the anatomical module 2000, including the vasculature simulator module 2200, and/or one or more peripheral organ/systems simulator module 2300 of the anatomical module 2000. Adjustment of flow rate can be accomplished by control mechanisms. For example, the flow rate for fluid entering the vasculature simulator module 2200 can be controlled by a first resistance valve 48, also referred to as a body resistance valve. Preferably, the resistance valve 48 is an electrically adjustable fluid resistance valve which includes a linear stepper motor and a globe valve. The resistance valve 48 can be automatically adjusted in order to achieve the desired flow rate to the body. The flow rate for fluid entering the one or more peripheral organ/systems simulator module, i.e. the head, can be controlled by a second resistance valve 50, also referred to as a head resistance valve. The second resistance valve 50 is preferably an electrically adjustable fluid resistance valve which includes a linear stepper motor and a globe valve. The resistance valve 50 can be automatically adjusted in order to achieve the desired flow rate to the head.

Each pathway, i.e. the vasculature pathway and the one or more peripheral organ/systems pathways, contains one or more monitoring or detecting mechanisms. As show in FIG. 2, the vasculature pathway includes a first flow meter 52, also referred to as a body flow meter. The body flow meter 52 may be, for example, a paddle wheel flow meter, configured to convert volumetric flow rate to an electrical signal. The signal is used by the system controller (to be described later) to determine when changes to the flow resistance valve 48 settings are required in order to achieve the desired flow. The one or more peripheral organ/systems may include a second flow meter 54, also referred to as a head flow meter. The head flow meter 54 may also be a paddle wheel flow meter configured to convert volumetric flow rate to an electrical signal. The signal is used by the system controller to determine when changes to the second flow resistance valve 50 settings are required in order to achieve the desired flow. Fluid is then transported back to fluid reservoir 12. A check valve 56 ensures that the returning fluid flow enters into the fluid reservoir 12 while preventing backflow, i.e. reverse flow out of the fluid reservoir 12, replicating the actions of the anatomical veins.

Fluid may be drained from the cardiovascular simulator system 10 via a drain connector, such as a Schrader type quick disconnect valve 58. The valve 58 may be connected to a drainage hose or tubing (not shown) attached during the draining cycle operation. The fluid is preferably drained into a container, shown as a fluid holding container or jug 60.

Referring to FIG. 3, the cardiovascular simulator system 10 is shown with the pneumatics components. Air generator 100, described as compressor 100, is responsible for several functions within the cardiovascular simulator system 10. Air compressor 100 provides pressurized air flow to the cardiac simulator module 2100 through tubing 110 or 112. Specifically, pressurized air is supplied to the left atrium 2112, specifically the left atrium cavity 2124, and the left ventricle 2114, specifically the left ventricle cavity 2120. Control of air flow into the cardiac simulator module 2100, i.e. into the left atrium 2112, specifically the left atrium cavity 2124, and the left ventricle 2114, specifically the left ventricle cavity 2120, so as to allow each component to simulate a beating heart, is provided by one or more control mechanisms. Control of the left atrium 2112 can be accomplished using a valve, illustrated on FIG. 3 as an actuation solenoid valve 114, also referred to as an atrium actuation solenoid valve. When the atrium actuation solenoid valve 114 is energized, pressurized air from compressor 100 is admitted into the left atrium cavity 2124. Such action compresses the left atrium 2112. When the atrium actuation solenoid valve 114 is de-energized, pressure is released from the left atrium cavity 2124, allowing the left atrium 2112 to relax. A second actuation solenoid, referred to as a ventricle actuation solenoid valve 116 controls air into the left ventricle 2114. When the ventricle actuation solenoid valve 116 is energized, pressurized air from the compressor 100 is admitted into the left ventricle cavity 2120 that surrounds the left ventricle 2114. This action allows the left ventricle 2114 to compress and push out any fluid therein. When the ventricle actuation solenoid valve 116 is de-energized, pressure from the left ventricle cavity 2120 is released, allowing the left ventricle 2114 to relax. Such actions simulate physiological contractions, and thus heartbeat, of the left side of the heart. The pressurized air may also cause one or more portions of the cardiac module, such as the left ventricle 2114, to partially move about its axis to more accurately simulate the heartbeat. Such actions may also be accomplished in the right atrium 2116 and right ventricle 2118 (not shown). The left atrium 2112 and the left ventricle 2114 may be separated from the right atrium 2116 and right ventricle 2118 via a partition or wall 2121 (see FIG. 9), thus preventing fluid flow there between. The partition or wall 2121 between the left and right chambers maybe referred to as the cardiac septum 2121. One or more of the chambers may have fluid in/out tubing and/or openings, such as tubing 2123A, 2123B, or 2123C to allow fluid to flow in or out.

The air compressor 100 may be fluidly connected to the arterial compliance chamber 18 via tubing 118 in order to reduce the water level in the arterial compliance chamber 18. To aid in draining fluid from within the cardiovascular simulator system 10, the air compressor 100 may be fluidly connected to the fluid reservoir 12 via tubing 120. Fluid can be drained via drain disconnect valve 58, pumping pressurized air through the venous chamber 12, as well as arterial compliance chamber 18. Various control mechanisms for delivery of the pressurized air from the air compressor 100 is preferably utilized. A valve, referred to as a venous chamber venting valve 122 is used to control the amount of air, and therefore the pressure, to the venous chamber 12. For example, manipulation of the venous chamber venting valve 122 to release air pressure from the venous chamber 12 may be used when the average venous pressure is determined to be too high. A second valve, referred to as a venous chamber pressurization valve 124 can be used to admit pressurized air into the venous chamber 12 in order to, for example, increase the baseline venous pressure. Manipulation of the venous chamber pressurization valve 124 may also be used during the drain cycle to force pressurized air through the cardiovascular simulator system 10. The pressurized air that is forced through the cardiovascular simulator system 10 drives the fluid out via the drain disconnect valve 58.

A valve, referred to as an arterial chamber venting valve 126 is designed to affect the hydraulics of the arterial compliance chamber 18. Manipulation of the arterial chamber venting valve 126 releases air pressure from the arterial compliance chamber 18. This has the effect of allowing more water to enter into the chamber, thereby reducing the air volume. This also has the effect of reducing the hydraulic compliance of the arterial compliance chamber 18. A second valve, the arterial chamber pressurization valve 128 can be used to control air flow into the arterial compliance chamber 18. Manipulation of the arterial chamber pressurization valve 128 admits pressurized air into the arterial compliance chamber 18. Admission of the pressurized air drives any fluid out of the arterial compliance chamber 18. As fluid is driven out, air volume increases within the arterial compliance chamber 18 and increases the compliance of the arterial compliance chamber 18. The arterial chamber pressurization valve 128 may further be used in the drain cycle to force pressurized air through the cardiovascular simulator system 10. As the pressurized air moves throughout the cardiovascular simulator system 10, any fluid within the cardiovascular system 10 is driven out through the drain disconnect valve 58.

Figure 4A:
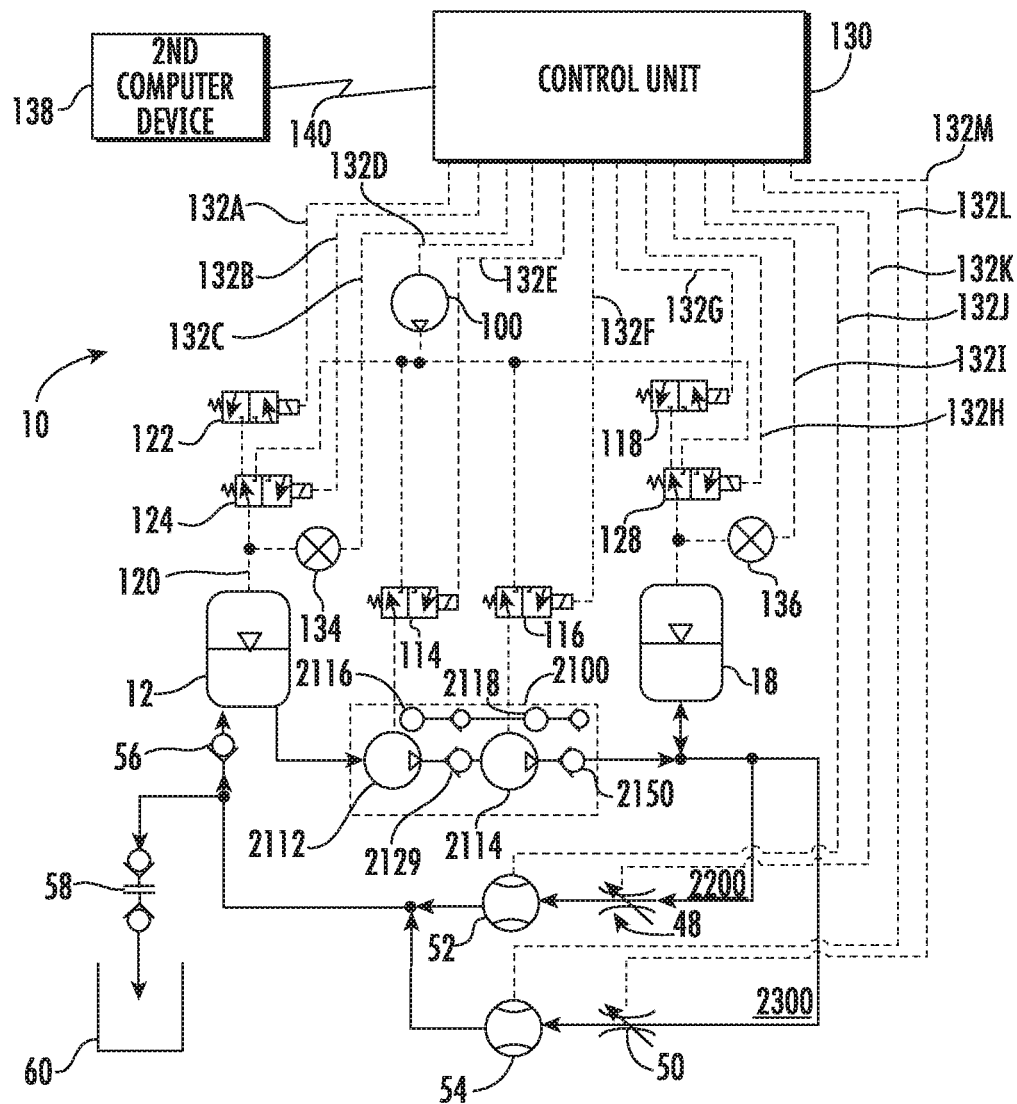
FIG. 4A is a block diagram, as shown in FIG. 3, including the general electronic circuitry schematic associated with the simulator system in accordance with an illustrative example of the present invention.

The cardiovascular simulator system 10 is designed to allow for control of various parameters to be run automatically. Such control allows the cardiovascular system to function more efficiently and accurately in order to represent blood flow and/or other physical characteristics as required. Referring to FIG. 4A, a control unit 130 is electronically connected to various components of the cardiac system through connector members 132A-132M, referred to generally as connector member 132. The connector member 132 may be wireless connection using, for example, blue tooth technology, or may be hardwired, such as computer cables using USB (Universal Serial Bus) connection. The control unit 130 is preferably a computer having the necessary hardware for processing capability, storage capability and any necessary software to drive or control the functioning of various components, and may include, for example, logic boards such as printed circuit boards with the necessary integrated circuitry, central processing units, RAM, ROM, and/or hard drives. The control unit 130 may simply be a printed circuit board with the necessary integrated circuitry. The control unit 130 must be designed to process various system parameters measured by the body flow meter 52 and the head flow meter 54. Additionally, the cardiovascular simulator system 10 may contain sensors 134, 136, and 137. Sensor 134, also referred to as the venous pressure sensor, is a pressure sensor configured to convert gauge pressure reading of the fluid chamber 12 into an electrical signal. The signal can be transmitted to the system control unit 130 where a determination of adjustment to the fluid chamber 12 pressurization can be made. Alternatively, sensor 134 in the venous chamber or reservoir 12 may only be monitored, acting simply as a passive sensor, or be used to only vent the venous chamber instead of pressurizing the chamber. Sensor 136, also referred to as the arterial pressure sensor, is a pressure sensor configured to convert the gauge pressure reading of the arterial compliance chamber 18 into an electrical signal. The signal can be transmitted to the system control unit 130 where adjustment to the pumping action of the cardiac simulator module 2100 to achieve various system pressures, i.e. to represent a predetermined systolic and diastolic pressure can be determined and/or made. Sensor 136 can be used to directly measure fluid pressure and not the pressure in the compliance chamber. While the sensor 136 may be used to measure pressure in an area representing the subclavian, sensor 136 may be placed anywhere close by, such as in the tubing representing the ascending aorta or left subclavian, see FIG. 1C or 1D. A third sensor, sensor 137 may be used as an active sensor. Sensor 137 may be placed at the left atrium 2112 to provide monitoring of the pressure at the cardiac, or other region, of interest. This sensor 137 may be used to control the centrifugal pump if utilized. The control unit 130 may further be configured to use command values to affect other system operations through, for example, control of 1) body flow resistance valve 48 settings, 2) head flow resistance valve 50 settings, 3) the speed profile of the compressor 100, and 4) the timing and actuation of the atrium actuation solenoid valve 114 and the ventricle actuation solenoid valve 116. In addition, the control unit 130 may be programmed to control the use of the compressor 100 in conjunction with the arterial chamber venting valve 126 and the arterial chamber pressurization valve 128 to modify levels of fluid in the arterial compliance chamber 18, thereby modifying the compliance. The control unit 130 may contain an information display, such as an LCD screen, to provide an interface with the user to allow for manipulation of one or more parameters.

Figure 27A:
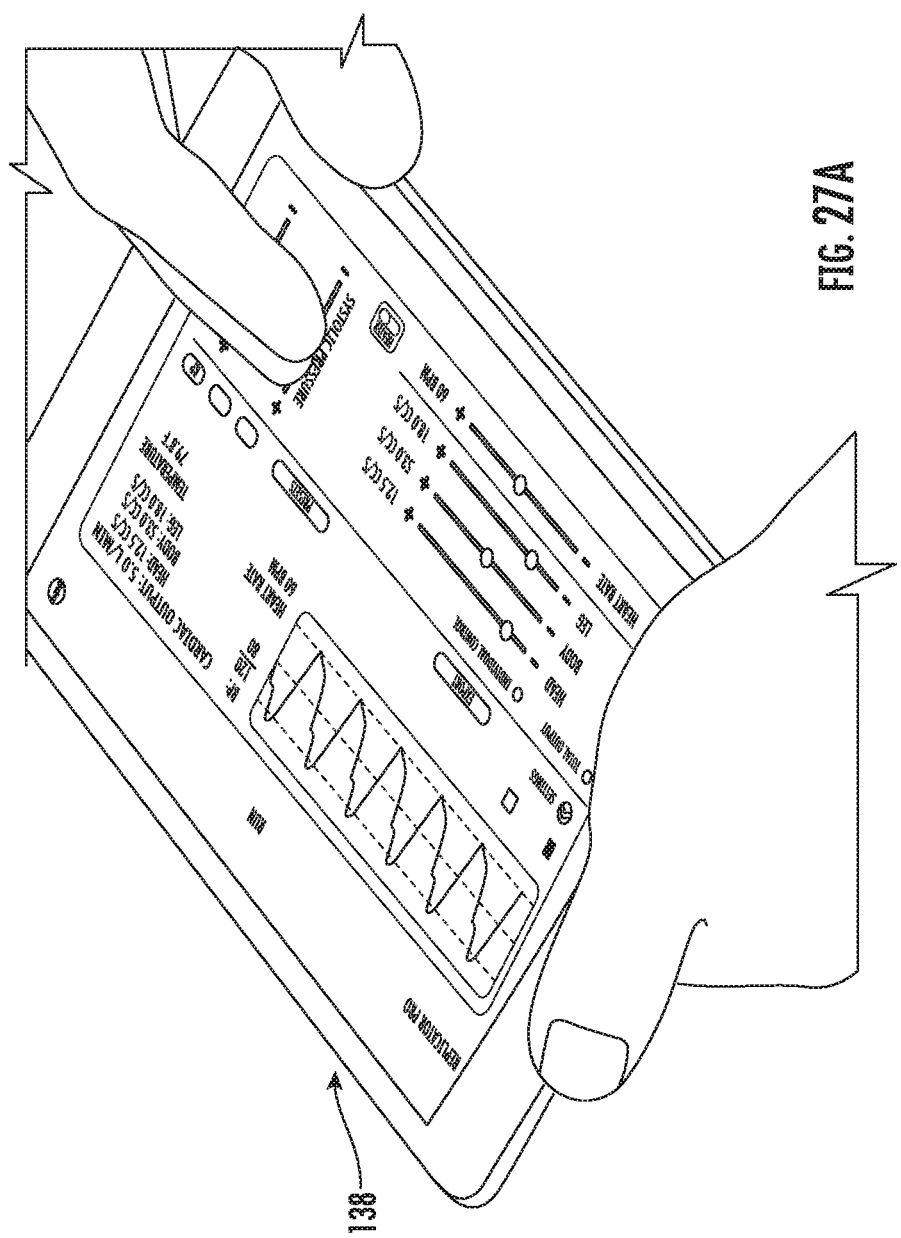
FIG. 27A is an illustrative example of a hand-held tablet computer.
Figure 27B:
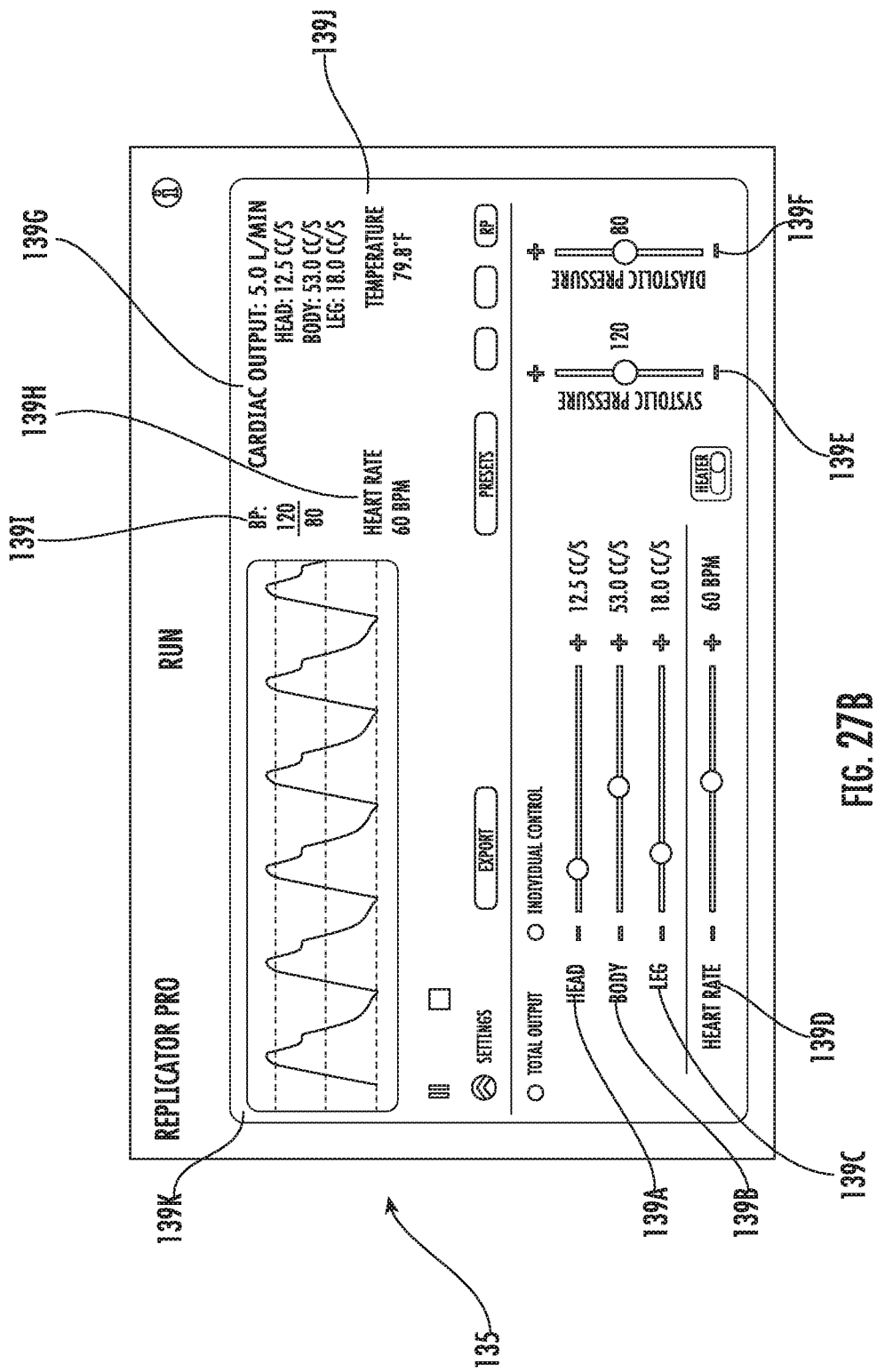
FIG. 27B is a screen shot of the tablet shown in FIG. 27A, providing an illustrative example of a graphic user interface (GUI) which allows a user to adjust one or more system parameters.

A second computer device, illustrated as a tablet computer 138 (see FIG. 27A for illustration of a hand-held tablet 138), may be used in conjunction with the control unit 130. The tablet computer 138 may contain the necessary hardware, such as a processor and memory, as well as the necessary software to provide a user interface to monitor one or more operations of the system and to adjust any settings. The tablet computer 138 may be electronically connected to the control unit 130 by wireless or hardwire connection 140 (FIG. 4A). Preferably, the connection 140 is wireless, using, for example, blue tooth technology. However, the connection 140 may be via cable connections, such as cables using USB connection. FIG. 27B illustrates a screen shot 135 of the tablet 138, providing an illustrative example of the graphic user interface (GUI). The GUI provides various graphical icons and visual indicators that allow the user to adjust one or more parameters and view the corresponding results of the adjustments, including adjustments of fluid flow to head 139A, body 139B, leg 139C, heart rate adjustments 139D, manipulation of system systolic pressure 139E or diastolic pressure 139F, visual indicators for cardiac output valves 139G, heart rate 139H, blood pressure (BP) 139I, temperature 139J, or an electrocardiogram (EKG) print out 139K.

Figure 27C:
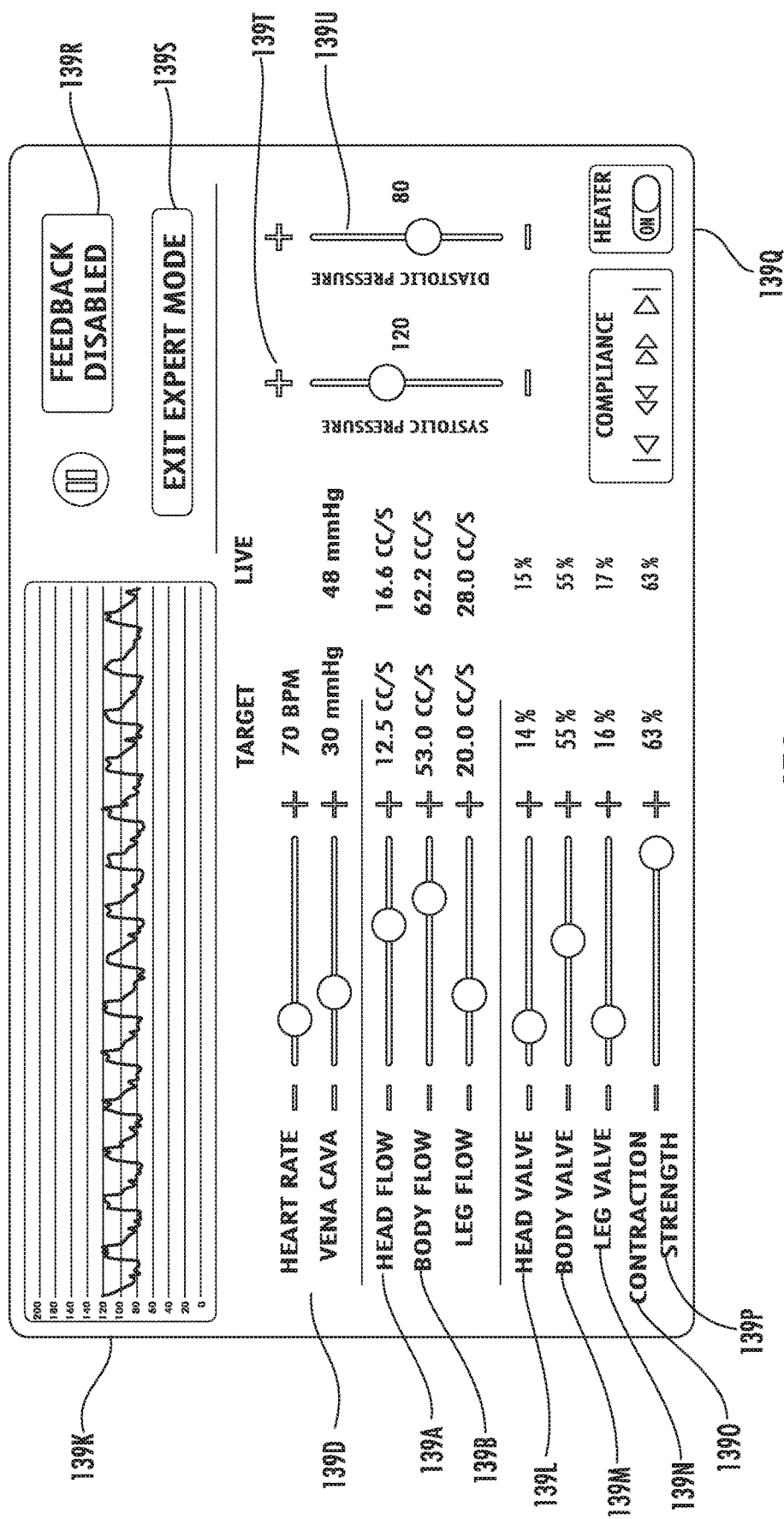
FIG. 27C is a screen shot of the tablet shown in FIG. 27A, providing an illustrative example of the Expert Mode.

FIG. 27C illustrates the Expert Mode configuration. The Expert Mode provides a user with additional predetermined icons and visual indicators that allow the user to adjust additional parameters and view the corresponding results of the adjustments, including head valve 139L, body valve 139M, leg valve 139N, contraction 139O, strength 139P, control of the heater, i.e. on/off, 139Q, feedback disabled 139R, and exit the expert mode 139S. Using the feedback disabled 139R, the user can disable the active feedback loops, which may be desired if a parameter meets a desired set point. The expert mode 139S mode allows the user to control specific hemodynamic features. Accordingly, the Expert Mode, as illustrated, adds the feature of controlling 1) Head, Body, and Leg resistor controls from 0-100%, 2) Pressure control of Inferior Vena Cava, 3) Pump Speed or Contraction Strength of the cardiac pumping, and 4) Disable or Enable feedback control. Disabling feedback may be needed for resistor control for Head, Body, and Leg resistor controls from 0-100%. When feedback is disabled, the Expert Mode also allows for Increase/Decrease of the arterial compliance chamber pressurization (Increase/Decrease of percent duration of cycle). There is only an active stop to the decrease. If compliance is reduced too much, i.e., fluid is increased in the compliance chamber 18 such that the fluid level switch is triggered, it stops further decrease in compliance (compliance chamber filling).

Figure 4B:
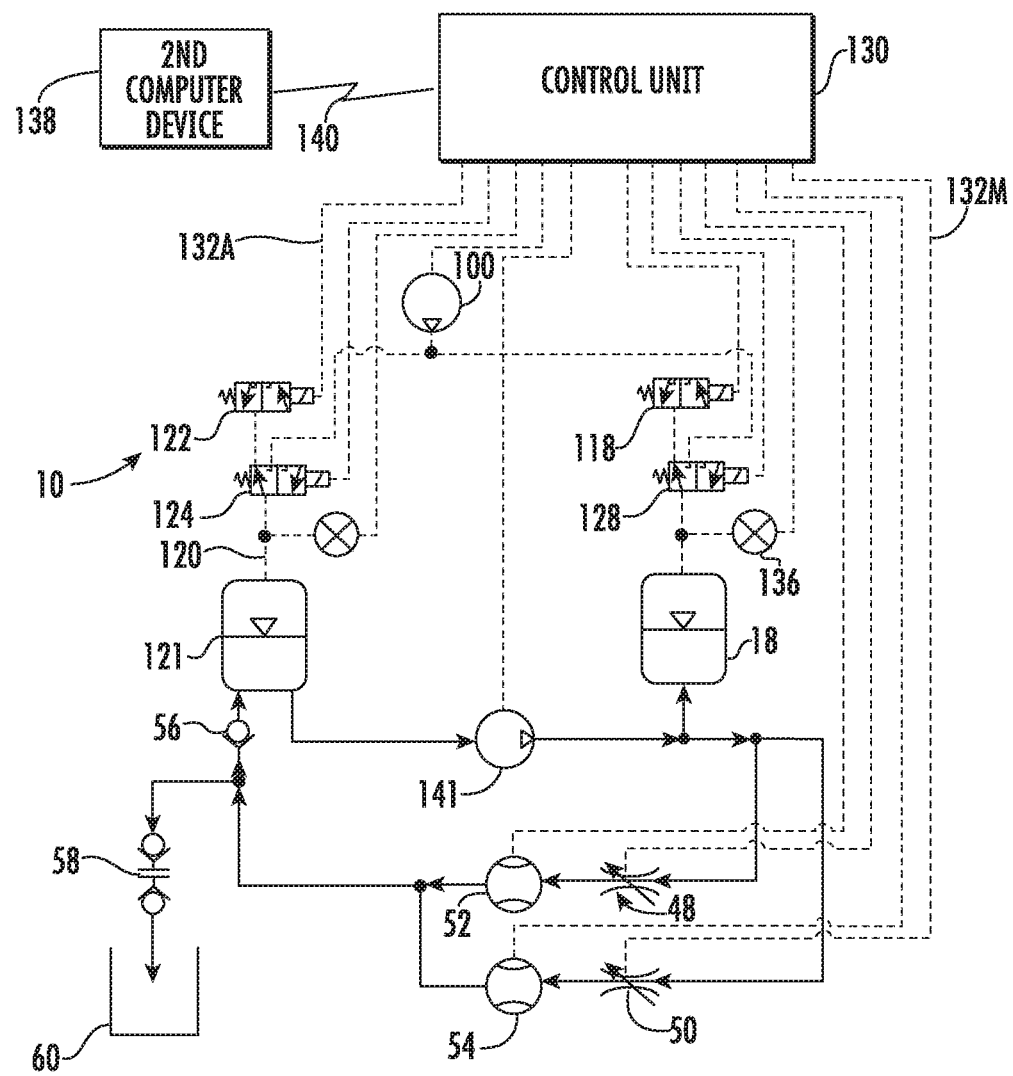
FIG. 4B is a block diagram showing an illustrative example of the present invention using a pump to represent the cardiac module.

FIG. 4B illustrates the cardiovascular simulator system 10 in which the cardiac simulator module 2100 uses an electrically driven pump 141. The pump 141 provides similar pulsatile flow characteristics as that of the anatomical heart model previously described. Such an embodiment could provide similar physiological pressure and flow characteristics with potentially lower cost, smaller size, higher reliability, or more controllable flow characteristics.

Fluid stored within the fluid reservoir 12 is passed through the system using the compressor 100 to push pressurized air into the fluid reservoir 12. The action of the pressurized air allows the cardiac simulator module 2100 to function like a heart muscle of a human or animal by contracting and expanding, forcing fluid representing blood flow to travel within the vasculature simulator module 2200. The control unit 130 is designed to supply pulses of pressurized air to the cardiac simulator module 2100. Fluid pressures and fluid dynamics/flows are created by the pumping action of the cardiac module itself. The fluid is pushed out of the fluid reservoir 12 and enters the anatomical module 2000, which represents oxygenated blood returning from the lungs, not used in the presently described system, and flows through (tubing and structures that represent) the inferior vena cava, into the right atrium, right ventricle, pulmonary arteries, and then right and left pulmonary veins.

The left atrium 2112 fills with fluid, and the pressure of the fluid, measured at the systolic side of the circuit, is controlled by the control unit 130 to be in the minimal normal range for diastolic pressure of a human heart (50-80 mm HG). The actual blood pressure of 120/80 (systolic/diastolic) obtained by the system is a combination function of the fluid flow volume (simulated by manipulation of the control unit 130 in relationship to the cardiac simulator module), the cardiac simulated heart rate, arterial compression, ventricular compression (or ejection fraction, simulated as the amount of fluid ejected out of the atrium chamber or ventricle chamber), the capillary resistance (simulated effects by the manipulation of the resistance valve) and the vascular tonometry or tension (simulated effects by the manipulation of the compliance chamber 18).

The cardiovascular simulator system 10 is designed to independently adjust for systolic and diastolic values using various combinations of parameters which affect the systolic and diastolic numbers to varying degrees. The value of the diastolic pressure can be manipulated to above or below the normal ranges to simulate various disease states using the control module. In addition to any of the components described previously, the control unit 130 may include one or more circuit boards, such as a control printed circuit board (PCB) and a second PCB for control of voltage sensing. A power source, which may include a battery, powers the entire cardiac simulation system 10. Initiated by the control module 130, the left atrium 2112 is contracted. Contraction of the left atrium is controlled by the compressor 100, which controls when and how much pressurized air is forced into the left atrium 2112. The pressurized air generated flows through tubing and enters the left atrium cavity 2124. The air causes the reduction of the volume within the left atrium chamber 2112. Reduction of the volume results in fluid being expelled through the mitral valve 2129 and into the left ventricle 2114.

The pressurized air generated travels through tubing into the left ventricle cavity 2120. The pressurized fluid causes a reduction of volume within the left ventricle chamber 2114, resulting in the expulsion of fluid through the synthetic aortic valve 2150 and into the aortic arch 2203. Because of the feedback systems utilized, the cardiovascular simulation system is configured to regulate various physiological parameters. The pressure of the fluid can be set, for example, within the range of normal physiological representative systolic/diastolic pressures. For example, the cardiovascular simulator system 10 may include set points of: 1) default 120 mmHg representing systolic pressure, 2) default 80 mmHg, representing diastolic pressure, 3) default 10 mmHg, representing venous pool pressure, 4) blood flow of, default 12 mL/second, representing the average cephalic flow (total head flow), 5) blood flow, default 80 mL/second, representing the average thoracic aorta flow, and 6) fluid temperature, default 98.6 degrees Fahrenheit. These values or set points may also be changed to represent non-default values. The physiological parameter set points are adjustable by a user. In addition, the system uses the feedback controls to automatically compensate for changes in the set points.

The conditions can be manipulated by the control unit 130 to change the corresponding pressure, volume flow rate, ejection fraction, or combinations thereof, as the fluid moves through the entire system. The fluid ejected from the left ventricle chamber is under pressure and flows through tubing which represents or simulates various portions of the vascular anatomy, such as the vertebral arteries, the left common carotid artery, and the right common carotid artery. Fluid also flows down to the descending aorta and into the right iliac artery 2218 and the left iliac artery 2220. As such, the cardiovascular simulator system 10 is configured to regulate the average of systolic and diastolic pressure by adjusting the volume of pressurized air produced by the compressor 100 and used to compress the atrium and ventricle. Time varying air flow rates within a cycle (as opposed to constant flow) is preferably generated. Regulation of the pressure difference between representative systolic and diastolic pressures are accomplished by adjusting the volume of air (and thus the hydraulic compliance) of the arterial compliance chamber 18. Adjusting the resistance valves provides regulation of the representative cephalic and thoracic flow. The flow meters are preferably positioned in the representative venous portion of the system rather than the representative arterial portion. Therefore, flows are more continuous than pulsatile at that point and adjustments to average flow rates, rather than ejection fractions and peak flow rates, can be used.

With regards to the heating of the fluid, heater surface temperature and replicator fluid temperature can be determined and controlled via the control unit 130 to heat the fluid to the desired temperature, while ensuring that the heater surface temperature does not exceed a predefined limit.

Eventually, all fluid is directed back to the fluid reservoir 12 in which the flow rate is adjusted. Vascular tension can be simulated and adjusted through several mechanisms, such as through the use of compliance and resistance valves, and through the molded vasculature simulator module 2200 representing the arteries having various durometer values. Although not illustrated, fluid flow may be directed to the periphery organ/system module, i.e. the head 2302 and its representative vasculature tubing. If used as part of the cardiac simulation system 10, the head 2302 may be secured to the support structure frame 142A and 142B through the head support structure 150. The head 2302 may contain a quick connect connector to quickly and easily connect/disconnect to/from the support structure frame 142A and 142B, and can be capable of angular translation. Fluid is then returned to the tubing representing the pulmonary anatomy, and eventually back into the cardiac simulator module 2100 to start a new cycle.

While not described in detail, the right atrium 2116 and ventricle 2118 may be adapted to function in the same manner and have the same features as described for the left atrium 2112 and ventricle 2114.

The body resistance valve 48, the head resistance valve 50, the body flow meter 52 and the head flow meter 54 may be housed in housing structures. The compliance adjusting valves, such as the venous chamber venting valve 122, the venous chamber pressurization valve 124, the arterial chamber venting valve 126, and/or the arterial chamber pressurization valve 128 may be stored in a housing structure.

As described previously, abnormal heart conditions can be simulated by varying the force, duration, and frequency of the air burst generated by the atrium/ventricle assemblies through commands sent from the control unit and adjustments to various structures within the system to cause such changes to occur.

Figure 18:
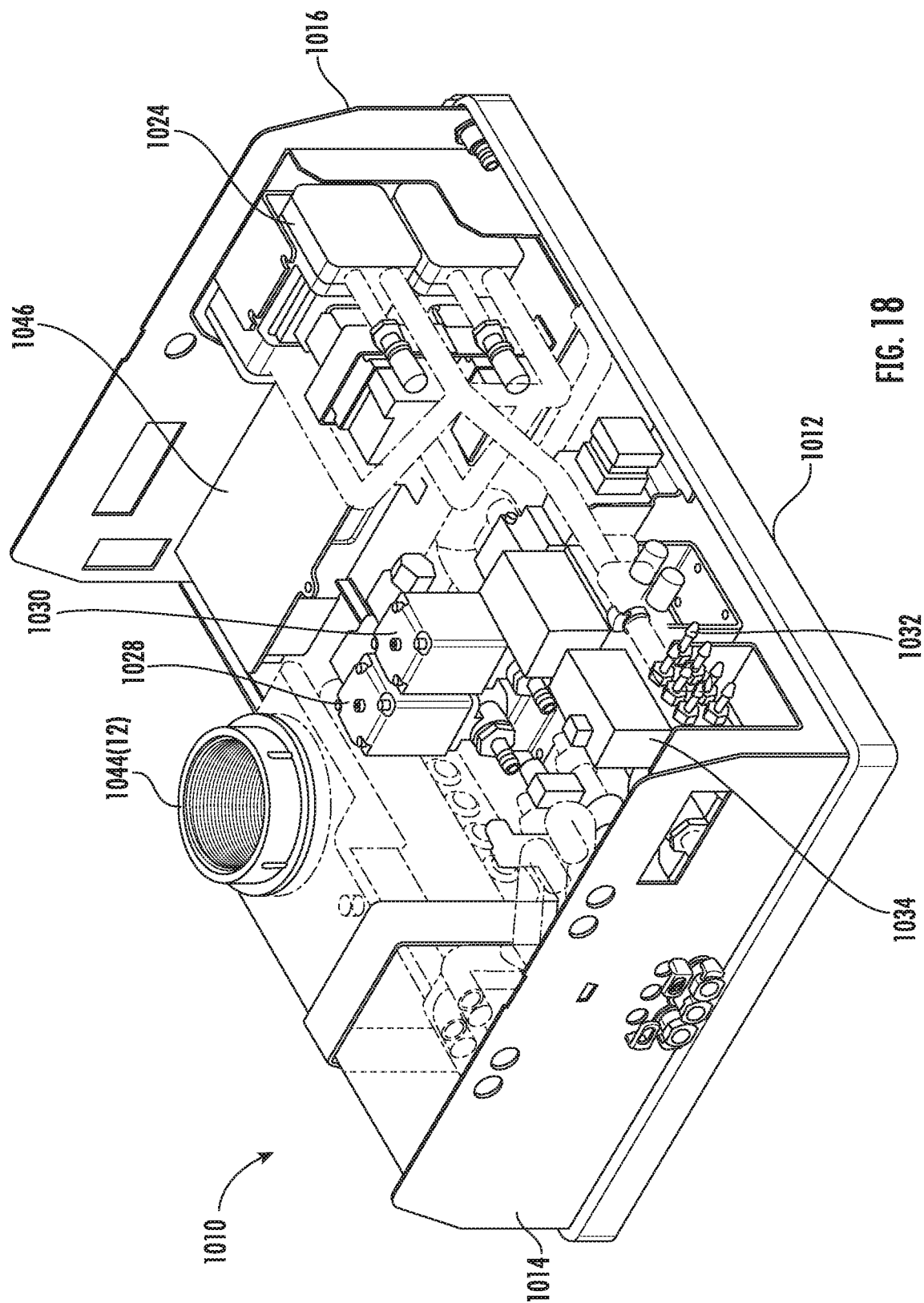
FIG. 18 is a perspective view of the hardware component module.
Figure 19:
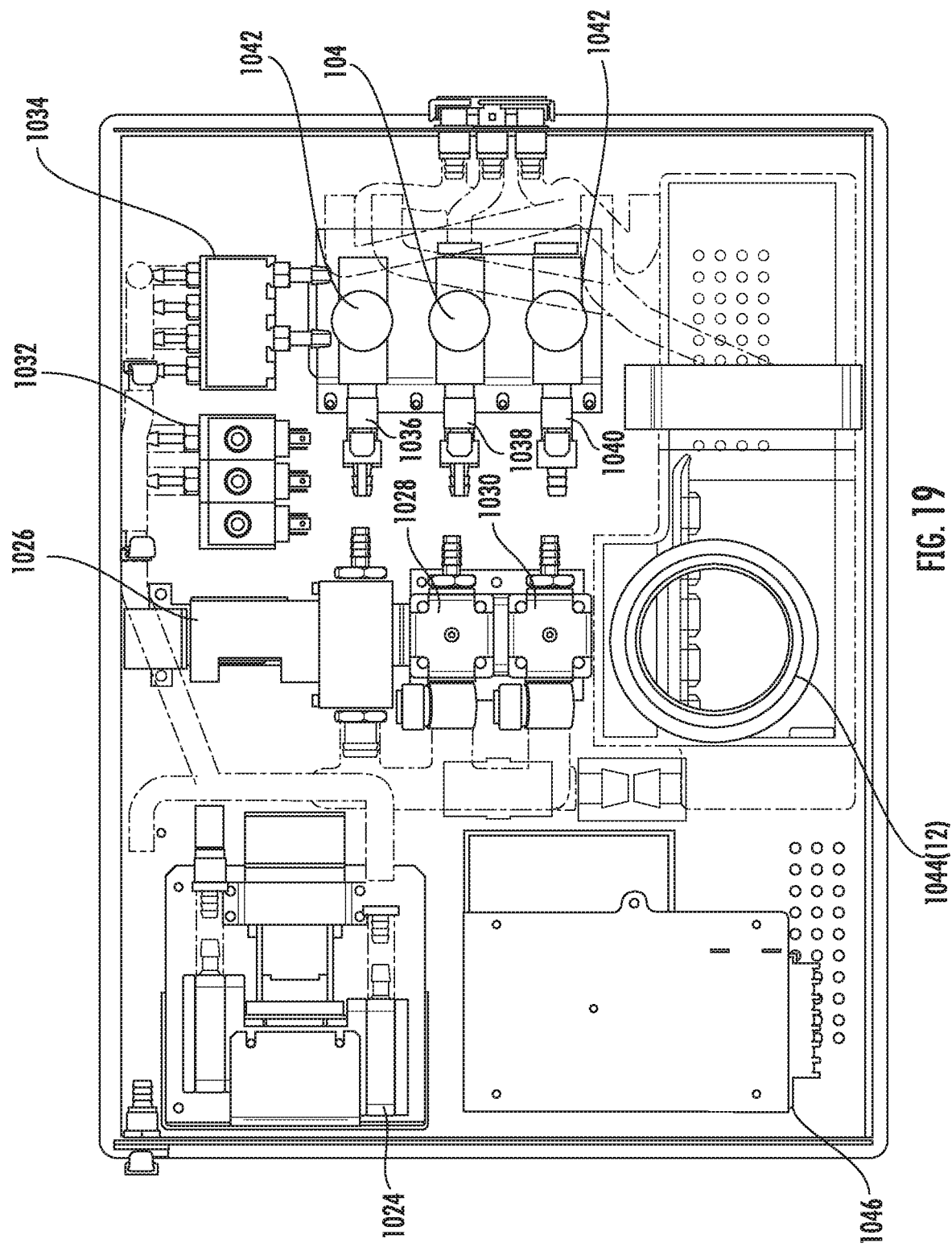
FIG. 19 is a top view of the hardware component module.

In order to allow the cardiovascular simulator system 10 to be imaged with X-rays, the electromechanics are placed in hardware component module 1010, see FIGS. 1A and 1C, separated from the cardiac simulator module 2100, a vasculature simulator module 2200, and one or more peripheral organ/systems simulator module 2300. FIGS. 18 and 19 provide an illustrative example of the hardware component module 1010 associated with the cardiovascular simulator system 10 shown in FIGS. 1A and 1B. The hardware component module 1010 may comprise a bottom wall 1012, and side walls 1014 and 1016. Side walls 1018 and 1020, and top wall 1022, see FIG. 1A, are removed. The interior region portion stores and secures one or more hardware components, including diaphragm pumps 1024, resistance valves 1026, 1028, and 1030, solenoids 1032, 1034, flow meters 1036, 1038, and 1040, filter(s) 1042, fluid reservoir 1044, and a power supply and circuit board storage unit 1046 which stores the control unit circuit board and power supply. While the components of the hardware component module 1010 have been given a reference number "1000" for general description, the actual component referenced may correspond to a previously described component, but given a different number. For example, the resistance valves 1026-1030, the solenoids 1032-1034, or flow meters 1036-1040 may correspond to any of the resistance valves, solenoids, or flow meters described above.

Figure 20:
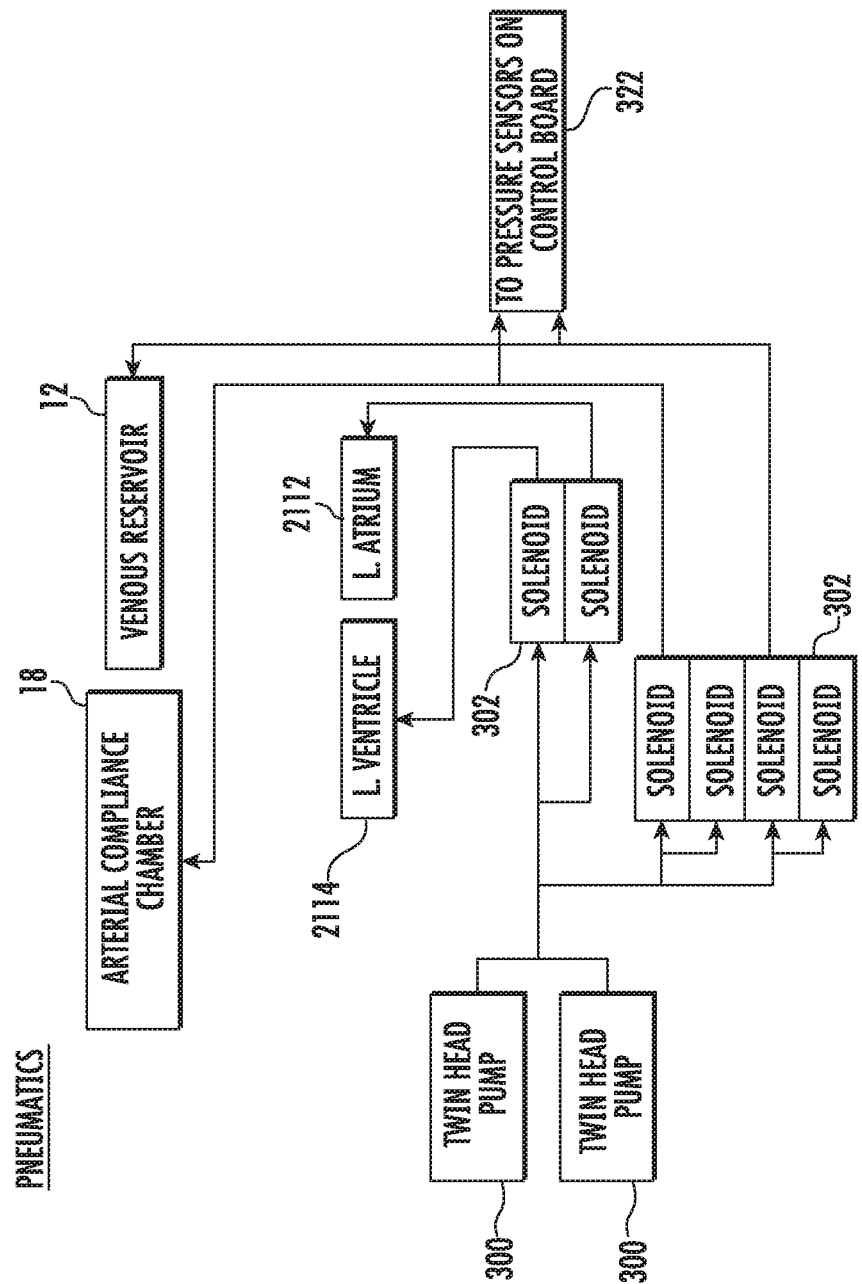
FIG. 20 is a block diagram of an illustrative embodiment of a pneumatic circuit schematic associated with the simulator system.
Figure 21:
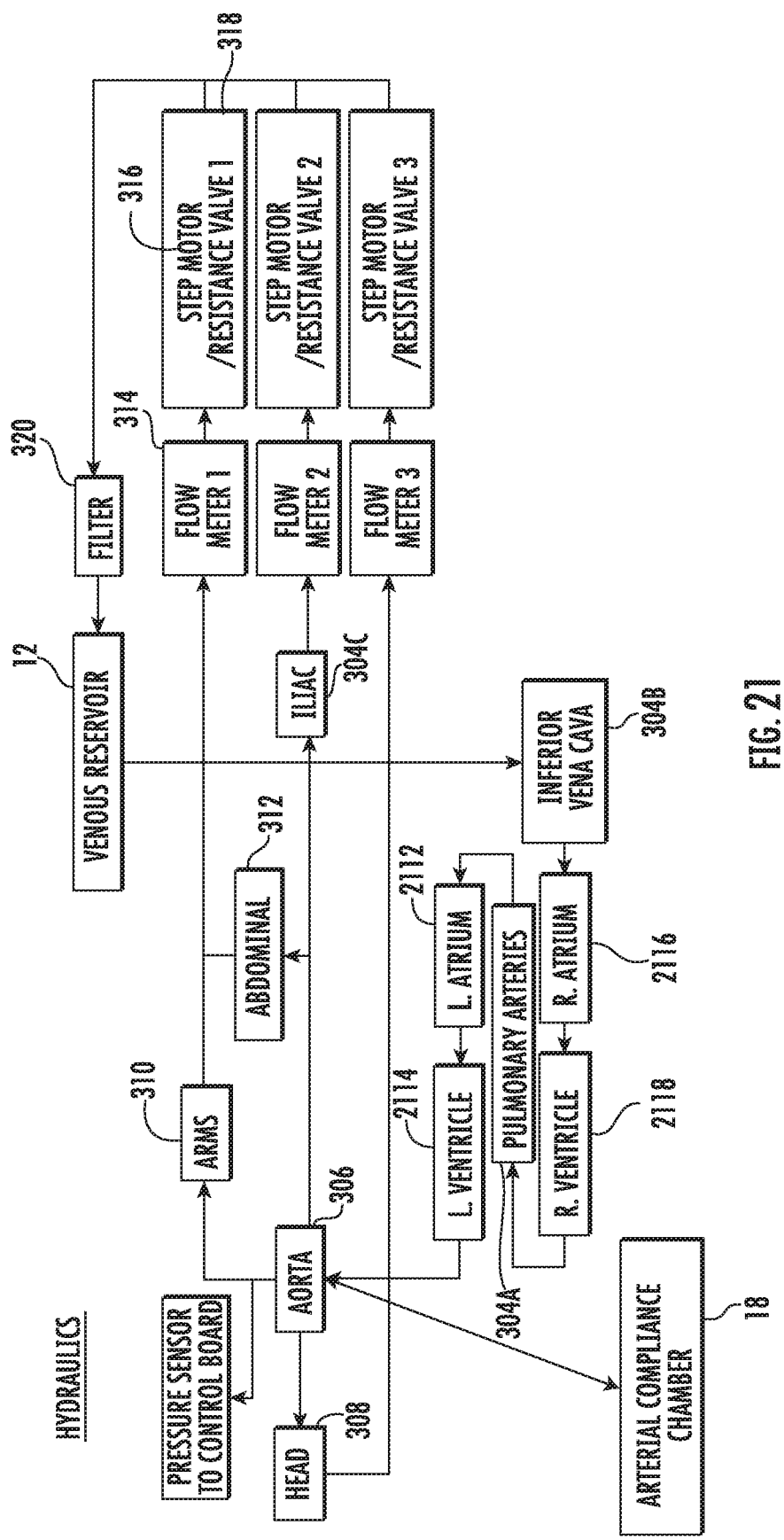
FIG. 21 is a block diagram of an illustrative embodiment of a hydraulic circuit schematic associated with the simulator system.
Figure 22:
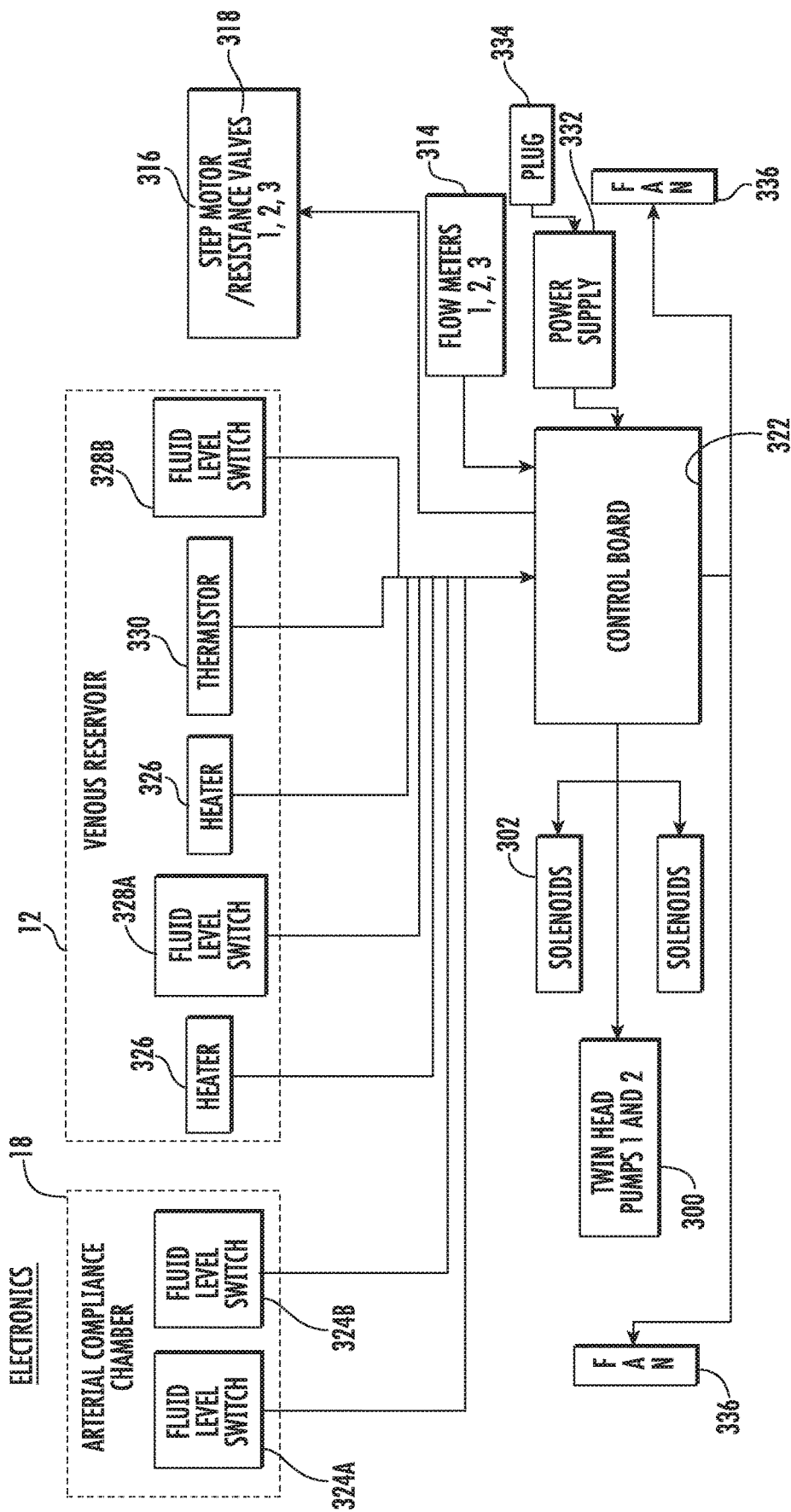
FIG. 22 is a block diagram of an illustrative embodiment of an electronic circuitry schematic associated with the simulator system in accordance with an illustrative example of the present invention.
Figure 23A:
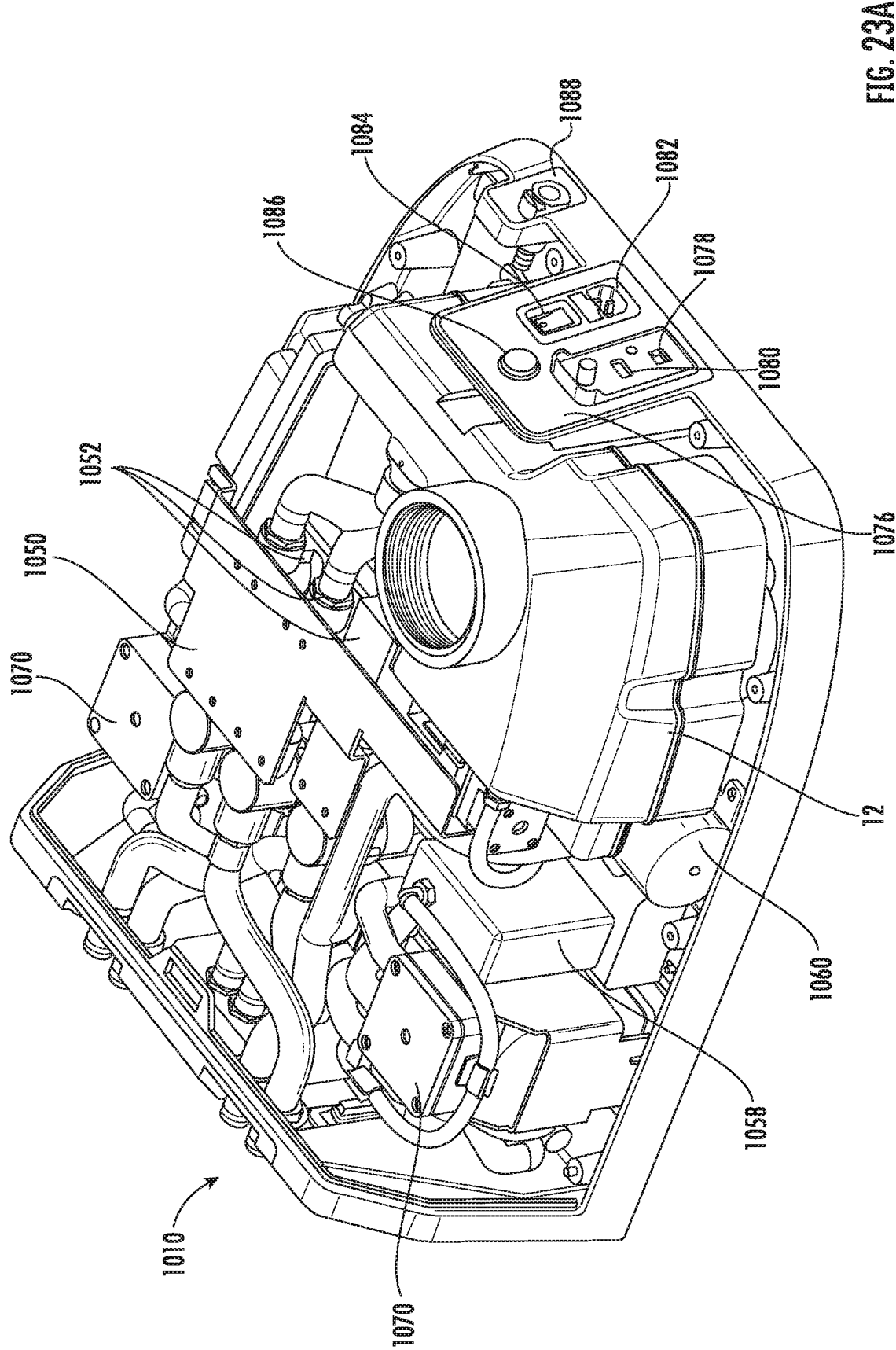
FIG. 23A is a perspective view of the hardware component module associated with the cardiovascular simulation system illustrated in FIG. 1C or FIG. 1D.
Figure 23C:
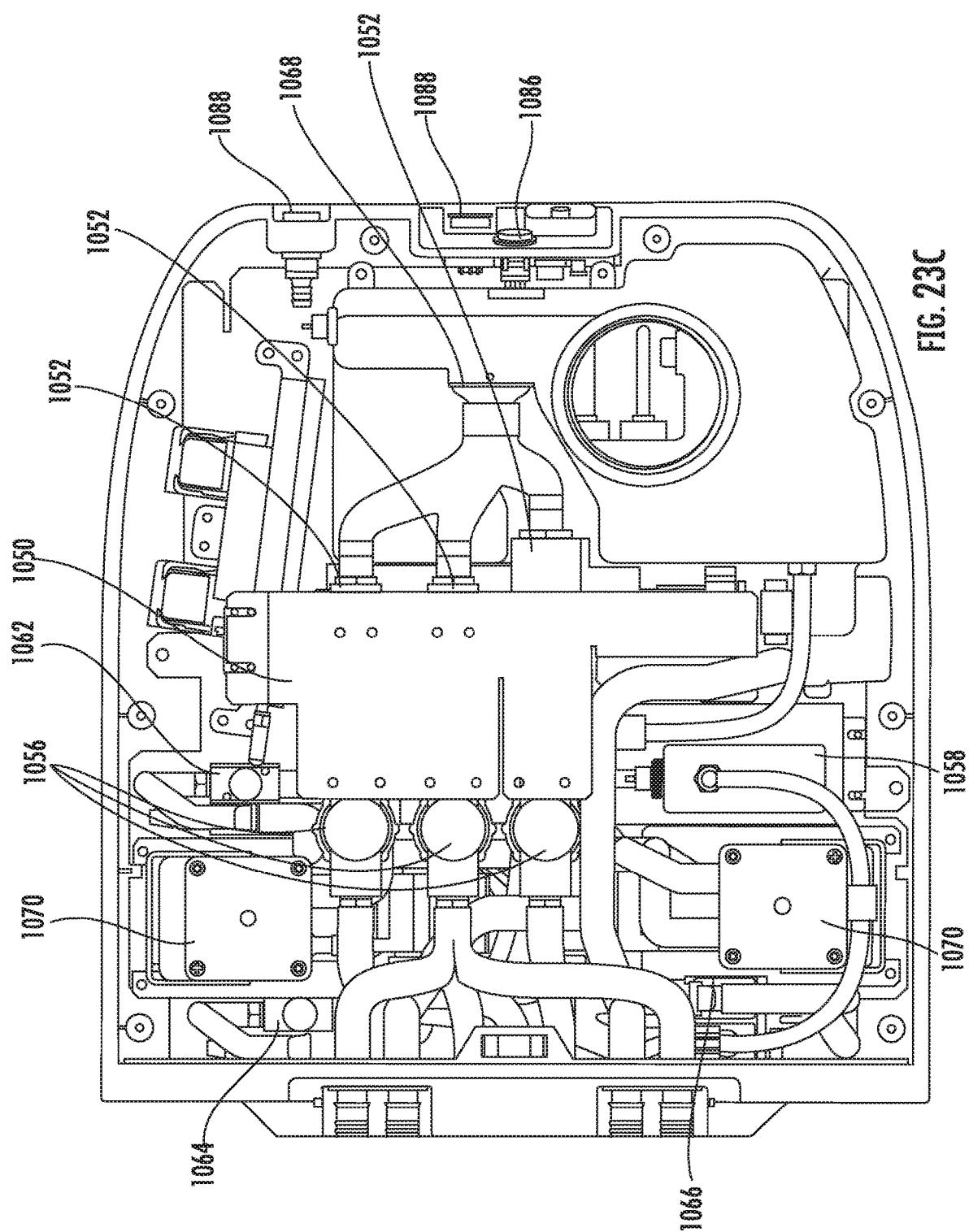
FIG. 23C is a top view of the hardware component module associated with the cardiovascular simulation system illustrated in FIG. 1C or FIG. 1D.
Figure 23D:
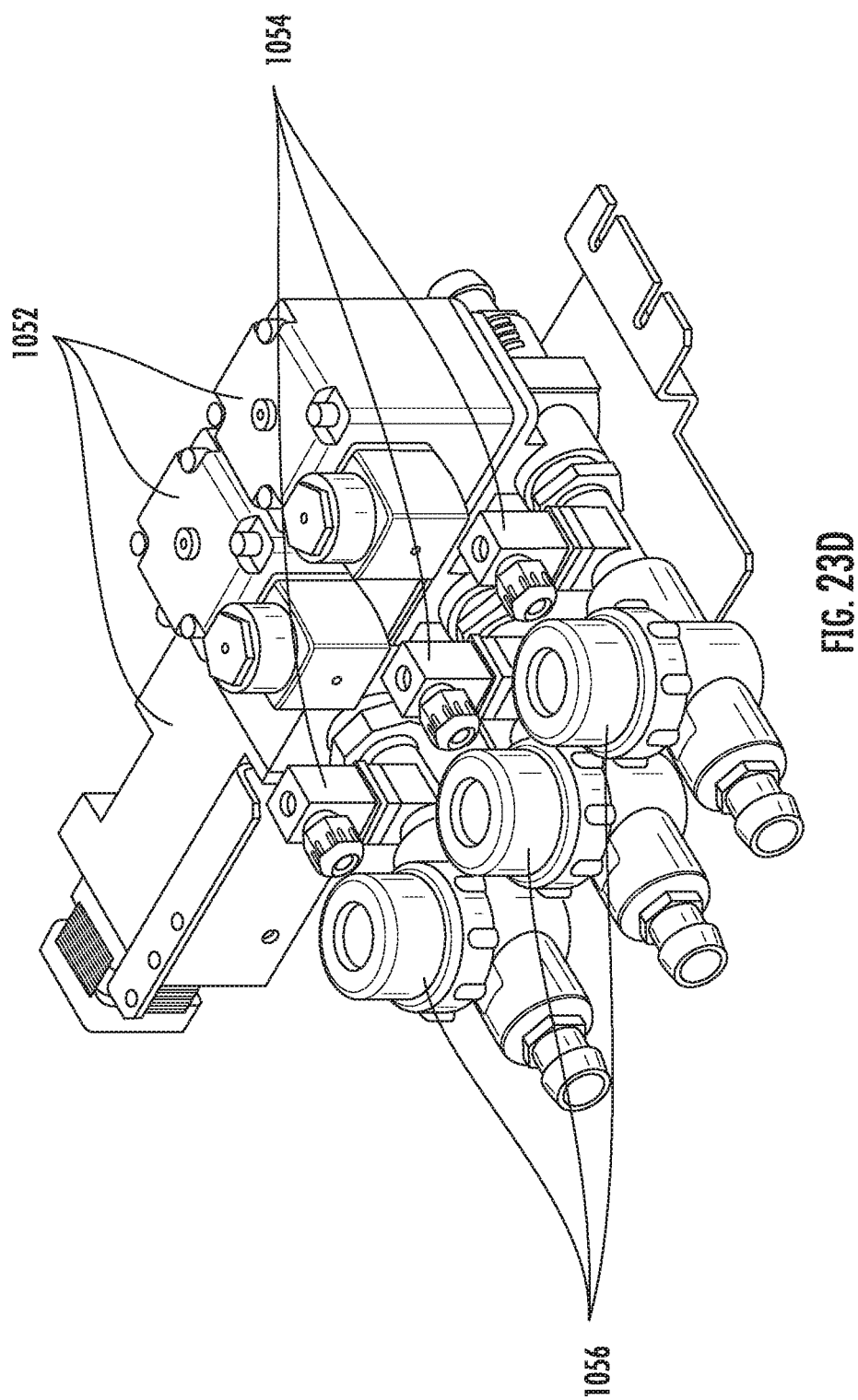
FIG. 23D illustrates the assembly bracket removed from the hardware module.

Referring to FIGS. 20-22, schematic diagrams of the pneumatics (FIG. 20), hydraulics (FIG. 21), and electronics (FIG. 22) are provided as an illustrative example. The systems described in the figures provide for a vasculature module that uses three (3) anatomical flow paths (head, gut/arms, and legs). In addition, there is also an anatomical flow path (inferior vena cava) returning flow to the cardiac module. As shown in FIG. 20, pressurized air may be provided and driven within the cardiovascular simulator system 10 via twin pumps 300, such as twin head pumps or diaphragm pumps. The pumps 300, which may be controlled by use of solenoids 302, provide pressurized air to functionally act upon the left atrium 2112, left ventricle 2114, the compliance chamber 18, or venous reservoir (fluid reservoir) 12. FIG. 21 illustrates the flow of liquid fluid, simulating blood flow within the cardiovascular simulator system 10. Fluid from the venous reservoir (fluid reservoir) 12 provides fluid flow within the replica components associated with the body, such as the right ventricle 2118, the right atrium 2116, the left atrium 2112, and the left ventricle 2114, via pulmonary arteries 304A, inferior vena cava 304B, and iliac 304C, to the aorta 306, the head 308, arms 310 and abdominal area 312. Fluid flow may also be directed from the arterial compliance chamber 18 to the aorta 306 via compliance connection 2242. Fluid flow may be controlled via flow meters 314, which control the functioning of a step motor 316 or resistance valve 318. A filter 320 may be used to filter incoming liquid back into the venous reservoir 12. As illustrated in FIG. 22, the control board 322, which can be a computer or simply an integrated circuit board, controls pumps 300, the arterial compliance chamber fluid level switches, high 324A and low 324B, and various functions of the venous reservoir 12, such as heater 326, fluid level switches, high 328A and low 328B, and thermistor 330. The unit may be powered by a power supply 332, such as a battery or a plug 334 to a wall. To prevent overheating, one or more fans 336 may be utilized.

FIGS. 23A-23D provide an illustrative example of the hardware component module 1010 associated with the cardiovascular simulator system 10 shown in FIGS. 1C and 1D. The hardware component module 1010 may comprise a bottom wall 1012, and side wall 1014, and a hardware component module cover 1048 (See FIG. 1C, removed in FIGS. 23A-23C). The interior region stores and secures one or more hardware components, including a components assembly bracket 1050 which holds or stores one or more resistors 1052, one or more flow meters 1054, and one or more filters 1056, see FIG. 23D. The interior region also includes an overflow tank/chamber 1058, a centrifugal pump 1060, a venous reservoir (fluid reservoir) 12, venous reservoir solenoids 1062, a circuit board storage unit 1046 which stores the control unit circuit board and power supply, arterial compliance chamber solenoids 1064, pneumatic/cardiac solenoids 1066, a check valve 1068, pumps 1070, various tubing 1072 for transporting or move fluids, and tube threading 1074 to connect to tubing extending outside hardware component module 1010. In one embodiment, instead of the arterial compliance chamber having a high or low fluid level sensor, the arterial compliance chamber may be connected via tubing to the overflow chamber 1058. The overflow chamber 1058 may include a fluid level sensor 324C. The hardware component module 1010 may also comprise a BNC output connector 1076 to obtain EKG trigger signal timed to the cardiac cycle, a USB/B input connector 1078 to facilitate direct (wired connection) communication with a tablet 138 (should wireless communication mechanisms, such as BLUETOOTH, fail), USB/A output connector 1080 to charge devices, such as tablet 138, power plug 1082, On/Off switch 1084, emergency stop 1086, and drain tube 1088. The venous reservoir (fluid reservoir) 12 may contain a cap 1090 and a pressure sensor and fluid switch connection control unit 1092 (FIG. 1C).

Figure 24:
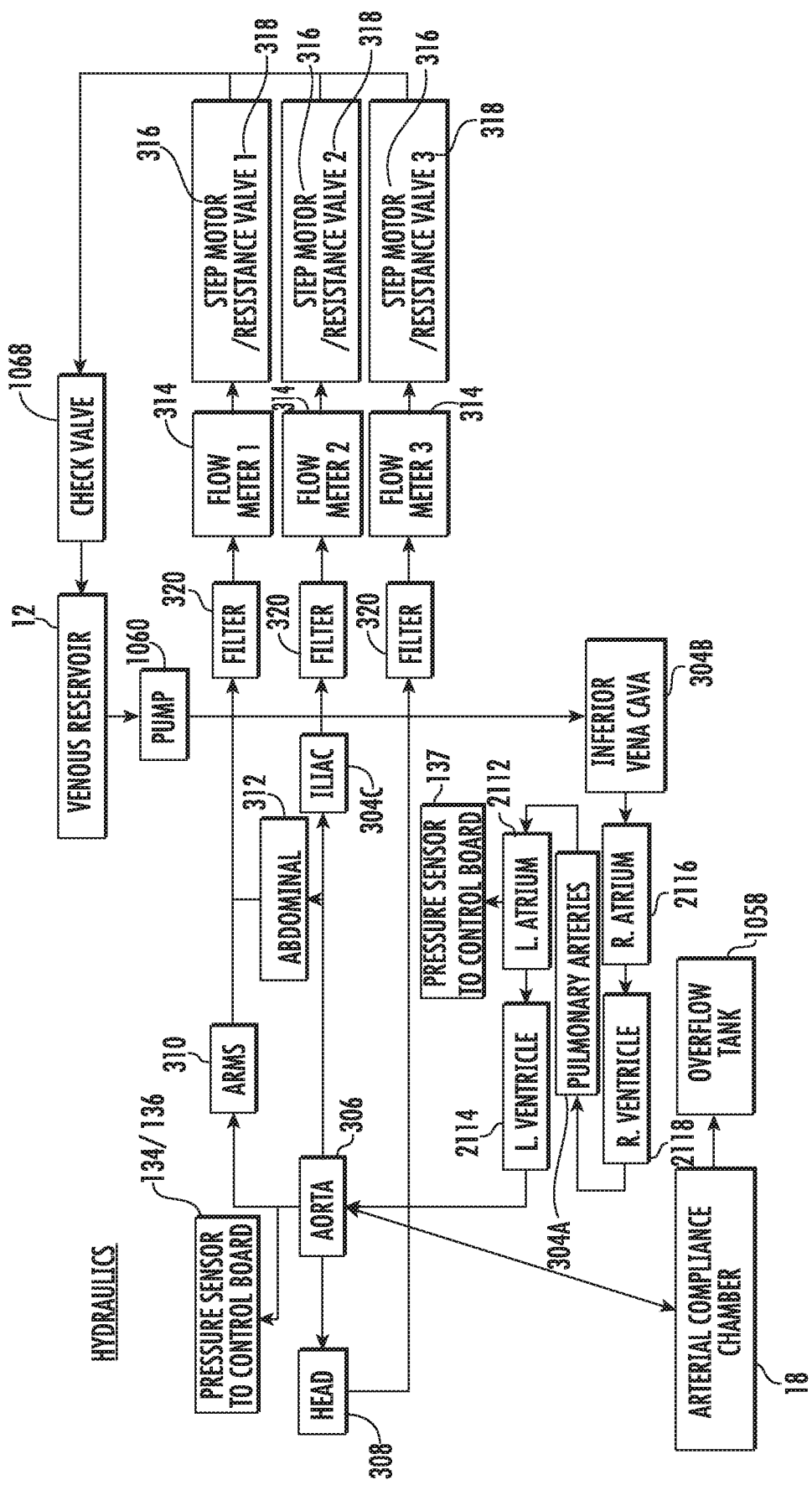
FIG. 24 is a block diagram of an illustrative embodiment of an hydraulic circuitry schematic associated with the cardiovascular simulation system illustrated in FIG. 1C or FIG. 1D.
Figure 25:
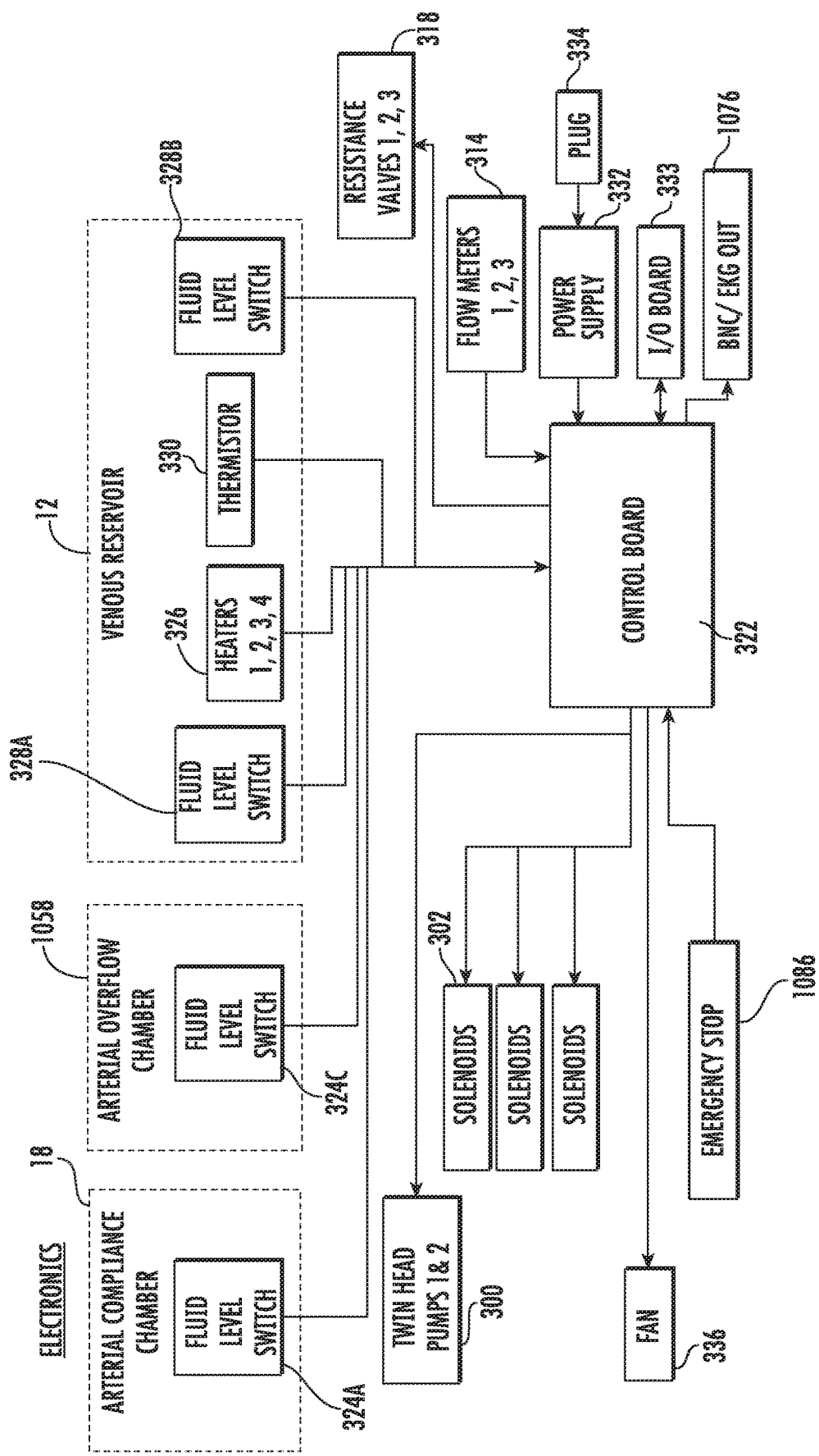
FIG. 25 is a block diagram of an illustrative embodiment of an electronic circuitry schematic associated with the cardiovascular simulation system illustrated in FIG. 1C or FIG. 1D.

FIGS. 24 and 25 illustrate schematic diagrams of the hydraulics (FIG. 24) and electronics (FIG. 25) associated with the cardiovascular simulator system 10 shown in FIGS. 1C and 1D. These diagrams contain the same components and same functions as that described in FIGS. 21 and 22, with the addition of the features described for the cardiovascular simulator system 10 shown in FIGS. 1C and 1D, including the check valve 1068, pump 1060, overflow tank/atrial overflow chamber 1058, pressure sensor to control board 137 in FIG. 24, and an arterial overflow chamber 1058 with fluid level switch 324C, I/O Board 333, BNC/EKG 1076, and emergency stop 1086 in FIG. 25.

Figure 26A:
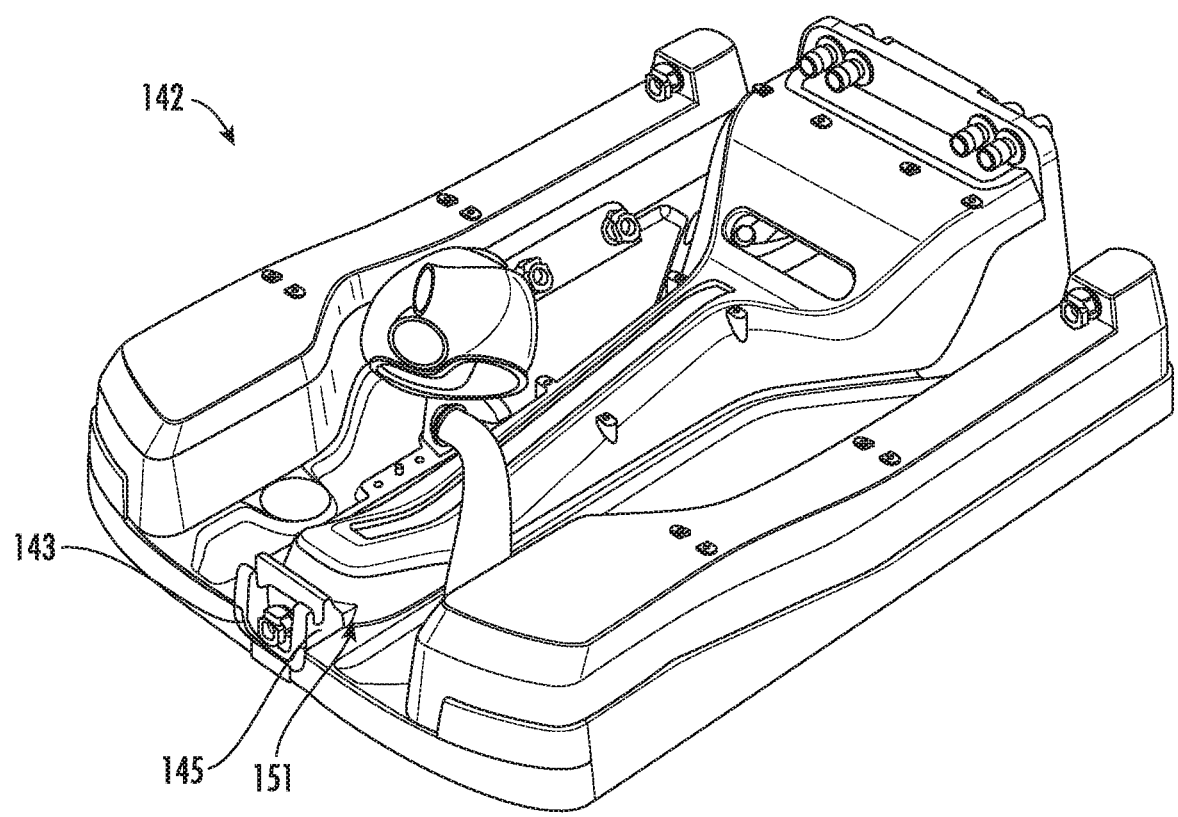
FIG. 26A is a perspective view of the support structure shown with several components of the cardiac simulator module and the vasculature simulator module removed to illustrate an adjustable peripheral organ/systems simulator module mount 143 shown in a retracted position.
Figure 26B:
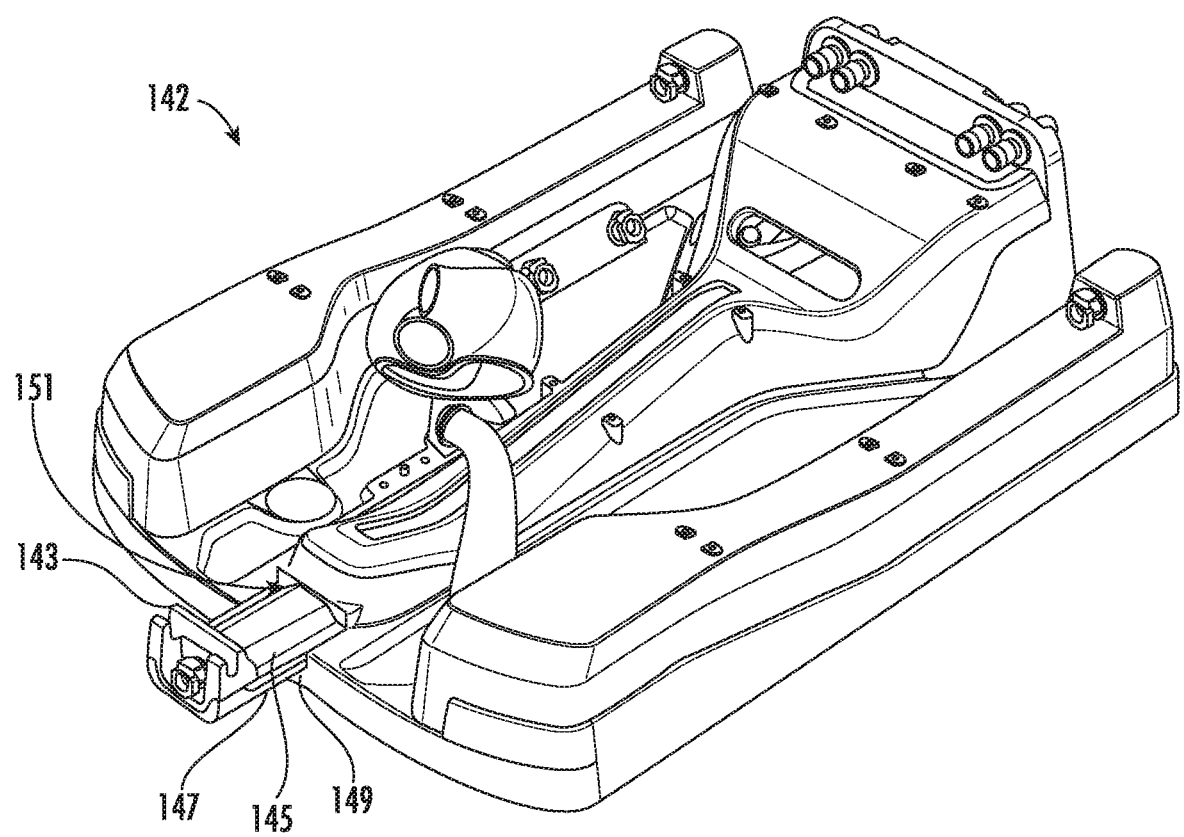
FIG. 26B is a perspective view of the support structure shown with several components of the cardiac simulator module and the vasculature simulator module removed to illustrate an adjustable peripheral organ/systems simulator module mount 143 shown in an extended position.

FIG. 26A and FIG. 26B illustrate the support structure 142 associated with the cardiovascular simulator system 10 shown in FIG. 1C and 1D, with several components removed. The support structure 142 comprises an adjustable peripheral organ/systems simulator module mount 143 having an elongated body 145 configured to secure the head 2302 thereto and slidably move in a linear movement to position the head in one or more positions: in a retracted position, FIG. 26A, or in an extended (or partially extended) position, FIG. 26B. The elongated body 145 may comprise a ridge 147 that engages with a channel 149 so the elongated body moves in and out of an opening. The adjustable peripheral organ/systems simulator module mount 143 provides better support and longer use of more complex aortic geometries.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A cardiovascular simulation system for simulating the cardiovascular system of a human or other mammal comprising:
    a control unit operatively coupled to a pneumatic feedback circuit configured to generate or move pneumatic fluid through said system and a hydraulic feedback circuit configured to move hydraulic fluid through said system, said pneumatic feedback circuit or said hydraulic feedback circuit is operatively connected to a cardiac simulator module, said computer based control unit configured to receive or process data obtained from sensors placed within said system and cause at least one component of said cardiac simulator module to function based on said data received or processed;
    at least one sensor placed within said system is constructed and arranged to detect or respond to changes in one or more parameters of said pneumatic feedback circuit;
    at least one sensor placed within said system is constructed and arranged to detect or respond to changes in one or more parameters of said hydraulic feedback circuit;
    said cardiac simulator module constructed and arranged for pneumatic pressurization comprising a plurality of chambers representing anatomical structures of a left side of a heart and optionally, a right side of said heart, each of said plurality of chambers defined by a wall, wherein at least one chamber wall of said plurality of chambers comprises a cavity constructed and arranged to receive a pneumatic fluid, said cavity separating said wall into an inner wall and an outer wall;
    said control unit providing physiologically accurate representation of a cardiovasculature system in normal or diseased states, whereby one or more operational parameters are automatically controlled without the need for manual adjustments.

2. The cardiovascular simulation system for simulating the cardiovascular system of a human or other mammal according to claim 1, wherein said cardiac simulator module comprises four chambers, wherein one chamber represents a left atrium, a second chamber represents a left ventricle, a third chamber represents a right atrium, and a fourth chamber represents a right ventricle.

3. The cardiovascular simulation system for simulating the cardiovascular system of a human or other mammal according to claim 2, wherein said left atrium chamber comprises said cavity within said wall.

4. The cardiovascular simulation system for simulating the cardiovascular system of a human or other mammal according to claim 2, wherein said left ventricle chamber comprises said cavity within said wall.

5. The cardiovascular simulation system for simulating the cardiovascular system of a human or other mammal according to claim 2, wherein said right atrium chamber comprises said cavity within said wall.

6. The cardiovascular simulation system for simulating the cardiovascular system of a human or other mammal according to claim 2, wherein said right ventricle chamber comprises said cavity within said wall.

7. The cardiovascular simulation system for simulating the cardiovascular system of a human or other mammal according to claim 2, wherein said left and right atrium chambers are anatomically modeled after a left and right atrium of a patient.

8. The cardiovascular simulation system for simulating the cardiovascular system of a human or other mammal according to claim 2, wherein said left and right ventricle chambers are anatomically modeled after a left and right ventricle of a patient.

9. The cardiovascular simulation system for simulating the cardiovascular system of a human or other mammal according to claim 1, wherein said cardiac simulator module is made of a soft plastic material.

10. The cardiovascular simulation system for simulating the cardiovascular system of a human or other mammal according to claim 1, further including a pneumatics module pneumatically connected to at least one chamber of said plurality of chambers representing said left side of said heart, or said right side of said heart.

11. The cardiovascular simulation system for simulating the cardiovascular system of a human or other mammal according to claim 1, wherein said pneumatics module is configured to provide compressed air to at least one chamber of said plurality of chambers representing said left side of said heart, or said right side of said heart.

12. The cardiovascular simulation system for simulating the cardiovascular system of a human or other mammal according to claim 1 further including at least one resistance valve configured to adjust the flow rate of a fluid within said system.

13. The cardiovascular simulation system for simulating the cardiovascular system of a human or other mammal according to claim 12, wherein said at least one resistance valve is an electrically adjustable fluid resistance valve.

14. The cardiovascular simulation system for simulating the cardiovascular system of a human or other mammal according to claim 1, wherein said control unit is configured to control the timing or speed of generation of pressurized air within said system.

15. The cardiovascular simulation system for simulating the cardiovascular system of a human or other mammal according to claim 1, wherein said pneumatic circuit or said hydraulic circuit is further linked to a vasculature system module comprising at least one tubing adapted to have characteristics of a human or other mammal artery or vein and fluidly connected to at least a portion of said cardiac system module.

16. The cardiovascular simulation system for simulating the cardiovascular system of a human or other mammal according to claim 1, further including a head module, said head module comprising a plurality of tubing suspended in a gel like material and fluidly connected to said cardiac system module or said vasculature system module.

17. The cardiovascular simulation system for simulating the cardiovascular system of a human or other mammal according to claim 16, further including at least one resistance valve constructed and arranged to adjust the flow rate of said fluid entering said head module.

18. The cardiovascular simulation system for simulating the cardiovascular system of a human or other mammal according to claim 1, further including at least one flow meter constructed and arranged for converting volumetric flow rate of a fluid not associated with a head region to an electrical signal or at least one flow meter constructed and arranged for converting volumetric flow rate of fluid associated with said head region to an electrical signal.

19. The cardiovascular simulation system for simulating the cardiovascular system of a human or other mammal according to claim 1, further including a pneumatic supply device constructed and arranged to provide pressurized or compressed air.

20. The cardiovascular simulation system for simulating the cardiovascular system of a human or other mammal according to claim 1, further comprising a fluid reservoir constructed and arranged to receive a fluid therein.

21. The cardiovascular simulation system for simulating the cardiovascular system of a human or other mammal according to claim 1, further comprising a heating device constructed and arranged to heat a fluid.

22. The cardiovascular simulation system for simulating the cardiovascular system of a human or other mammal according to claim 1, further including a fluid within said system.

23. The cardiovascular simulation system for simulating the cardiovascular system of a human or other mammal according to claim 1, further comprising a computer operatively connected to said control unit.

24. The cardiovascular simulation system for simulating the cardiovascular system of a human or other mammal according to claim 23, wherein said computer is wirelessly linked to said control unit.

25. The cardiovascular simulation system for simulating the cardiovascular system of a human or other mammal according to claim 1, further including an adjustable peripheral organ/systems simulator module.

26. The cardiovascular simulation system for simulating the cardiovascular system of a human or other mammal according to claim 1, wherein said chambers representing said left side of a heart, or optionally, said right side of said heart, are anatomically modeled after a patient.

27. The cardiovascular simulation system for simulating the cardiovascular system of a human or other mammal according to claim 1, wherein at least one chamber of said plurality of chambers includes a one-way valve.

28. A cardiovascular simulation system for simulating the cardiovascular system of a human or other mammal comprising:
a control unit configured to generate or move pneumatic fluid or hydraulic fluid through said system, said computer based control unit configured to receive or process data obtained from sensors placed within said system and cause at least one component of a cardiac simulator module to function based on said data received or processed;
at least one sensor placed within said system is configured to detect or respond to changes in one or more parameters of said pneumatic feedback circuit;
at least one sensor placed within said system is configured to detect or respond to changes in one or more parameters of said hydraulic feedback circuit;
said cardiac simulator module comprising a plurality of chambers representing Ere anatomical chambers of a heart, a left atrium chamber, a left ventricle chamber, a right atrium chamber, and a right ventricle camber, each chamber having a wall constructed and arranged to allow first fluid to pass from one chamber to another or allow fluid to remain within said chamber, in at least one chamber of said plurality of chambers, said wall comprises a cavity, said cavity constructed and arranged to receive a second fluid;
a vasculature system module comprising at least one tubing adapted to have characteristics of a human or other mammal artery or vein and fluidly connected to at least a portion of said cardiac system module;
said control unit providing physiologically accurate representation of a cardiovasculature system in normal or diseased states, whereby one or more operational parameters are automatically controlled without the need for manual adjustments.

29. The cardiovascular simulation system for simulating the cardiovascular system of a human or other mammal according to claim 28, further including a first fluid having one or more properties of blood.

30. The cardiovascular simulation system for simulating the cardiovascular system of a human or other mammal according to claim 28, wherein at least one chamber of said plurality of chambers includes a one-way valve.

* * * * *